United States Patent
Wang et al.

(10) Patent No.: US 6,476,016 B2
(45) Date of Patent: Nov. 5, 2002

(54) CYCLIC OXYGUANIDINE PYRAZINONES AS PROTEASE INHIBITORS

(75) Inventors: Aihua Wang, Jamison, PA (US); Bruce Edward Tomczuk, Collegeville, PA (US); Tianbao Lu, Kennett Square, PA (US); Richard M. Soll, Lawrenceville, NJ (US); John Curtis Spurlino, Downington, PA (US); Roger Francis Bone, Bridgewater, NJ (US)

(73) Assignee: 3-Dimensional Pharmaceuticals, Inc., Exton, PA (US)

(*) Notice: Subject to any disclaimer, the term of this patent is extended or adjusted under 35 U.S.C. 154(b) by 0 days.

(21) Appl. No.: 09/905,883

(22) Filed: Jul. 17, 2001

(65) Prior Publication Data
US 2002/0052357 A1 May 2, 2002

Related U.S. Application Data
(60) Provisional application No. 60/218,709, filed on Jul. 17, 2000.

(51) Int. Cl.[7] .................... C07D 413/12; C07D 413/14; A61K 31/495; A61K 31/496; A61K 31/501
(52) U.S. Cl. ............ 514/211.08; 514/183; 514/211.07; 514/211.01; 514/211.15; 514/217.05; 514/217.06; 514/212.08; 514/227.8; 514/229.2; 514/228.8; 514/232.2; 514/235.8; 514/236.2; 514/236.5; 514/236.8; 514/237.2; 514/252.02; 514/252.11; 514/252.12; 514/252.13; 514/252.14; 514/255.05; 540/601; 540/598; 540/467; 540/545; 540/544; 540/524; 540/525; 544/408; 544/405; 544/58.5; 544/58.2; 544/120; 544/121; 544/367; 544/357; 544/295; 544/238; 544/63; 544/66
(58) Field of Search .................... 544/405, 408, 544/58.2, 357, 63; 514/211.08, 183, 211.15, 212.08, 228.8, 236.2, 237.2, 252.12, 255.05; 540/524, 545, 598

(56) References Cited

U.S. PATENT DOCUMENTS

| | | | |
|---|---|---|---|
| 4,499,082 A | 2/1985 | Shenvi et al. | 514/2 |
| 4,727,064 A | 2/1988 | Pitha | 514/58 |
| 4,764,604 A | 8/1988 | Müller | 536/103 |
| 5,024,998 A | 6/1991 | Bodor | 514/58 |
| 5,466,811 A | 11/1995 | Alexander | 546/283 |
| 5,658,885 A | 8/1997 | Lee et al. | 514/19 |
| 6,037,356 A | 3/2000 | Lu et al. | 514/349 |
| 6,204,263 B1 | 3/2001 | Lu et al. | 514/235.8 |
| 6,326,492 B1 | 12/2001 | Wang et al. | 544/63 |

FOREIGN PATENT DOCUMENTS

| | | |
|---|---|---|
| EP | 0 363 284 B1 | 4/1990 |
| EP | 0 936 216 | 8/1999 |
| GB | 2 343 180 | 5/2000 |
| WO | WO 95/07291 A1 | 3/1995 |
| WO | WO 96/18644 | 6/1996 |
| WO | WO 97/01338 | 1/1997 |
| WO | WO 97/11693 | 4/1997 |
| WO | WO 97/30708 | 8/1997 |
| WO | WO 97/36580 | 10/1997 |
| WO | WO 97/40024 | 10/1997 |
| WO | WO 97/46207 | 12/1997 |
| WO | WO 98/09987 | 3/1998 |
| WO | WO 98/16547 | 4/1998 |
| WO | WO 98/23565 | 6/1998 |
| WO | WO 98/31670 | 7/1998 |
| WO | WO 99/11267 | 3/1999 |
| WO | WO 99/26926 | 6/1999 |
| WO | WO 99/59591 | 11/1999 |
| WO | WO 99/61442 | 12/1999 |
| WO | WO 99/64446 | 12/1999 |
| WO | WO 00/73302 | 12/2000 |

OTHER PUBLICATIONS

Barrett, A.J., "Proteinase inhibitors: potential drugs?" in *Enzyme Inhibitors as Drugs,* Sandler, M., ed., The MacMillan Press Ltd., London, England, pp. 219–229 (1979).

(List continued on next page.)

Primary Examiner—John M. Ford
(74) Attorney, Agent, or Firm—Sterne, Kessler, Goldstein & Fox, P.L.L.C.

(57) ABSTRACT

Cyclic oxyguanidine pyrazinone compounds are described, including compounds of the Formula I:

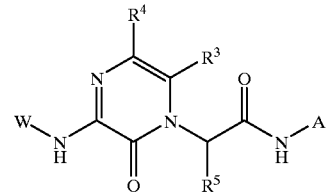

wherein $R^3$, $R^4$, $R^5$, W, and A are as set forth in the specification, as well as hydrates, solvates or pharmaceutically acceptable salts thereof. The compounds of the invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin. Compositions for inhibiting loss of blood platelets, inhibiting formation of blood platelet aggregates, inhibiting formation of fibrin, inhibiting thrombus formation, and inhibiting embolus formation are described. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents. Additionally, the compounds can be detectably labeled and employed for in vivo imaging of thrombi.

25 Claims, No Drawings

OTHER PUBLICATIONS

Brown, F.J., et al., "Design of Orally Active, Non–Peptidic Inhibitors of Human Leukocyte Elastase," *J. Med. Chem.,* 37:1259–1261, American Chemical Society (1994).

Claeson, G., "Synthetic peptides and peptidomimetics as substrates and inhibitors of thrombin and other proteases in the blood coagulation system," *Blood Coagulation and Fibrinolysis* 5:411–436, Rapid Communications (1994).

Coughlin, S.R., "Molecular Mechanisms of Thrombin Signaling," *Semin. Hematology 31(4):*270–277, W.B. Saunders Co. (1994).

Cuypers, H.T., et al., "Sulfhydryl Content of Bovine Eye Lens Leucine Aminopeptidase," *J. Biol. Chem.* 257:7086–7091, American Society of Biological Chemists, Inc. (1982).

Edwards, P.D., et al., "Design, Synthesis, and Kinetic Evaluation of a Unique Class of Elastase Inhibitors, the Peptidyl α–Ketobenzoxazoles, and the X–ray Crystal Strucutre of the Covalent Complex between Porcine Pancreatic Elastase and Ac–Ala–Pro–Val–2–Benzoxazole," *J. Am. Chem. Soc.* 114:1854–1863, American Chemical Society (1992).

Harker, L.A., "Strategies for inhibiting the effects of thrombin," *Blood Coagulation and Fibrinolysis* 5(*Suppl. 1*):S47–S58, Rapid Communications (1994).

Jeong, J.–H., et al., "Cyclic Guanidino–Sugars with Low $pK_a$ as Transition–State Analog Inhibitors of Glycosidases: Neutral Instead of Charged Species Are the Active Forms," *J. Amer. Chem. Soc.* 118:4227–4234, American Chemical Society (1996).

Kim, K.S., et al., "Preparation of Argatroban Analog Thrombin Inhibitors with Reduced Basic Guanidine Moiety, And Studies of Their Cell Permeability and Antithrombotic Activities," *Med. Chem. Res.* 6:377–383, Birkhäuser Boston, Inc. (1996).

Kimball, S.D., "Challenges in the development of orally bioavailable thrombin active site inhibitors," *Blood Coagulation and Fibrinolysis* 6:511–519, Rapid Science Publishers (1995).

Lee, S.–Li., et al., "Amidino and Guanidino substituted boronic acid inhibitors of trypsin–like enzymes," *CAPLUS* Accession No. 1997:594514, Abstract of U.S. Pat. 5,658,885 (1997).

Lefkovits, J. and Topol, E.J., "Direct Thrombin Inhibitors in Cardiovascular Medicine," *Circulation* 90:1522–1536, American Heart Association, Inc., (1994).

Mack, H., et al., "Design, Synthesis, and Biological Activity of Novel Rigid Amidino–Phenylalanine Derivatives as Inhibitors of Thrombin," *J. Enzyme Inhib.* 9:73–86, Harwood Academic Publishers (1995).

Ripka, W.C. and Vlasuk, G.P., "Chapter 8. Antithrombotics/ Serine Proteases," In: *Annual Reports in Medicinal Chemistry. vol. 32,* Bristol, J.A., ed., Academic Press, Inc., New York, NY, pp. 71–89 (1997).

Sauinier, M.G., et al., "An Efficient Method for the Synthesis of Guanidino Prodrugs," *Bioorg. & Med. Chem. Lett.* 4:1985–1990, Elsevier Science (1994).

Tapparelli, C., et al., "Synthetic Low–molecular weight thrombin inhibitors: molecular design and pharmacological profile," *Trends Pharmacol. Sci.* 14:366–376, Elsevier Science Publishers Ltd. (1993).

Sanderson, P.E.J., et al., "Efficaious, Orally Bioavailable Thrombin Inhibitors Based on 3–Aminopyridinone of 3–Aminopyrazinone Peptidomimetic Templates," *J. Med. Chem.* 41:4466–4474, American Chemical Society (1998).

CYCLIC OXYGUANIDINE PYRAZINONES AS PROTEASE INHIBITORS

CROSS-REFERENCE TO RELATED APPLICATIONS

This application claims the benefit, under 35 U.S.C. § 119(e), of the earlier filing date of U.S. Provisional Application No. 60/218,709, filed on Jul. 17, 2000, which is fully incorporated by reference herein.

BACKGROUND OF THE INVENTION

1. Field of the Invention

The present invention relates to novel compounds that function as proteolytic enzyme inhibitors, and particularly to a new class of thrombin inhibitors.

2. Background Art

Proteases are enzymes that cleave proteins at single, specific peptide bonds. Proteases can be classified into four generic classes: serine, thiol or cysteinyl, acid or aspartyl, and metalloproteases (Cuypers et al., *J. Biol. Chem.* 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerularnephritis. (Barret, in *Enzyme Inhibitors as Drugs*, Sandler, ed., University Park Press, Baltimore, (1980)). Additional proteases such as plasmin, C-1 esterase, C-3 convertase, urokinase, plasminogen activator, acrosin, and kallikreins play key roles in normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin, thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are expected to have an anti-inflammatory effect useful in the treatment of gout, rheumatoid arthritis and other inflammatory diseases, and in the treatment of emphysema. Chymotrypsin and trypsin are digestive enzymes. Inhibitors of these enzymes are useful in treating pancreatitis. Inhibitors of urokinase and plasminogen activator are useful in treating excessive cell growth disease states, such as benign prostatic hypertrophy, prostatic carcinoma and psoriasis.

The serine protease thrombin occupies a central role in hemostasis and thrombosis, and as a multifactorial protein, induces a number of effects on platelets, endothelial cells, smooth muscle cells, leukocytes, the heart, and neurons. Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, *Seminars in Hematology* 31(4):270–277 (1994)), and autoamplifies its own production through a feedback mechanism. Thus, inhibitors of thrombin function have therapeutic potential in a host of cardiovascular and non-cardiovascular diseases.

Factor Xa is another serine protease in the coagulation pathway. Factor Xa associates with factor Va and calcium on a phospholipid membrane thereby forming aprothrombinase complex. This prothrombinase complex then converts prothrombin to thrombin (Claeson, *Blood Coagulation and Fibrinolysis* 5:411–436 (1994); Harker, *Blood Coagulation and Fibrinolysis* 5 (Suppl 1):S47-S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3):1522–1536 (1994); Harker, *Blood Coagulation and Fibrinolysis* 5 (Suppl 1):S47-S58 (1994)).

In vivo diagnostic imaging methods for intravascular thrombi have been previously reported. These imaging methods use compounds that are detectably labeled with radioactive or paramagnetic atoms. For example, platelets labeled with the gamma emitter, In-111, can be employed as an imaging agent for detecting thrombi (Thakur, M. L. et al., *Thromb Res.* 9:345 (1976); Powers et al., *Neurology* 32:938 (1982)). The thrombolytic enzyme streptokinase labeled with Tc-99m has been proposed as an imaging agent (Wong, U.S. Pat. No. 4,418,052 (1983)). The fibrin-binding domains of *Staphylococcus aureus* derived protein A labeled with the gamma emitters, I-125 and I-131, have been proposed as imaging agents (Pang, U.S. Pat. No. 5,011,686 (1991)). Monoclonal antibodies having specificity for fibrin (in contrast to fibrinogen) and labeled with Tc-99m have been proposed as imaging agents (Berger et al., U.S. Pat. No. 5,024,829 (1991); Dean et al., U.S. Pat. No. 4,980,148 (1990)). The use of the paramagnetic contrasting agent, gadolinium diethylenetriaminepentaacetic acid in magnetic resonance imaging of patients treated by thrombolysis for acute myocardial infarction has been reported (De Roos, A. et al., *Int. J. Card. Imaging* 7:133 (1991)). Radiolabeled and paramagnetically labeled alpha-ketoamide derivatives have also been proposed as thrombus imaging agents (Abelman et al., U.S. Pat. No. 5,656,600).

A need continues to exist for non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states.

BRIEF SUMMARY OF THE INVENTION

The present invention is directed to novel cyclic oxyguanidine pyrazinones having Formula I (below). Also provided are processes for preparing compounds of Formula I, and pharmaceutical compositions comprising a compound of Formula I and one or more pharmaceutically acceptable carriers or diluents. The novel compounds of the present invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin, or are intermediates useful for forming compounds having antithrombotic activity. Also provided are methods of inhibiting or treating aberrant proteolysis in a mammal and methods of treating thrombosis, ischemia, stroke, restenosis or inflammation in a mammal by administering an effective amount of a compound of Formula 1.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

Also provided are methods of inhibiting or treating aberrant proteolysis in a mammal, and methods for treating myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; Down's syndrome; fibrin formation in the eye; and wound healing. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents.

The invention also includes a method for reducing the thrombogenicity of a surface in a mammal by attaching to the surface, either covalently or noncovalently, a compound of the invention.

In another aspect, the present invention includes compositions which are useful for in vivo imaging of thrombi in a mammal, comprising a compound of the present invention which is capable of being detected outside the body. Preferred are compositions comprising a compound of the present invention and a detectable label, such as a radioactive or paramagnetic atom.

In another aspect, the present invention provides diagnostic compositions which are useful for in vivo imaging of thrombi in a mammal, comprising a pharmaceutically acceptable carrier and a diagnostically effective amount of a compound or composition of the present invention.

In another aspect, the present invention includes methods which are useful for in vivo imaging of thrombi in a mammal.

In another aspect, the present invention includes processes for preparing an oxyguanidine compound of the invention.

DETAILED DESCRIPTION OF THE INVENTION

Compounds of the present invention include compounds of Formula I:

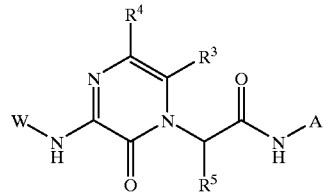

or a solvate, hydrate or pharmaceutically acceptable salt thereof; wherein:

W is hydrogen, $R^1$, $R^1OCO$, $R^1CO$, $R^1(CH_2)_2NHCO$, or $(R^1)_2CH(CH_2)_sNHCO$, wherein s is 0–4;

$R^1$ is
  $R^2$,
  $R^2(CH_2)_tC(R^{12})_2$, where t is 0–3, and each $R^{12}$ can be the same or different,
  $(R^2)(OR^{12})CH(CH_2)_p$, where p is 1–4,
  $(R^2)_2(OR^{12})C(CH_2)_p$, where p is 1–4,
  $R^2C(R^{12})_2(CH_2)_t$, wherein t is 0–3, and each $R^{12}$ can be the same or different, wherein $(R^{12})_2$ can also form a ring with C represented by $C_{3-7}$ cycloalkyl,
  $R^2CF_2C(R^{12})_2(CH_2)_q$, wherein q is 0–2, and each $R^{12}$ can be the same or different, wherein $(R^{12})_2$ can also form a ring with C represented by $C_{3-7}$cycloalkyl,
  $R^2CH_2C(R^{12})_2(CH_2)_q$, wherein q is 0–2, and each $R^{12}$ can be the same or different, wherein $(R^{12})_2$ can also form a ring with C represented by $C_{3-7}$ cycloalkyl,
  $(R^2)_2CH(CH_2)_r$, where r is 0–4 and each $R^2$ can be the same or different, and wherein $(R^2)_2$ can also form a ring with CH represented by $C_{3-7}$ cycloalkyl, $C_{7-12}$ bicylic alkyl, $C_{10-16}$ tricylic alkyl, or a 5- to 7-membered mono- or bicyclic heterocyclic ring which can be saturated or unsaturated, and which contains from one to three heteroatoms selected from the group consisting of N, O and S,
  $R^2O(CH_2)_p$, wherein p is 2–4,
  $(R^2)_2CF(CH_2)_r$, wherein r is 0–4 and each $R^{12}$ can be the same different, wherein $(R^{12})_2$ can also form a ring with C represented by $C_{3-7}$ cycloalkyl, $C_{7-12}$ bicyclic alkyl, $C_{10-16}$ tricyclic alkyl, or a 5- to 7-membered mono- or bicyclic heterocyclic ring which can be saturated or unsaturated, and which contains from one to three heteroatoms selected from the group consisting of N, O and S,

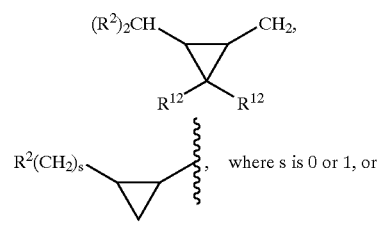

$R^2CF_2C(R^{12})_2$;

$R^2$ is
  phenyl, naphthyl, or biphenyl, each of which is unsubstituted or substituted with one or more of $C_{1-4}$ alkyl, $C_{1-4}$ alkoxy, halogen, hydroxy, $CF_3$, $OCF_3$, COOH, $CONH_2$, or $SO_2NH_2$,
  a 5- to 7-membered mono- or a 9- to 10-membered bicyclic heterocyclic ring or non-heterocyclic ring which can be saturated or unsaturated, wherein the heterocyclic ring contains from one to four heteroatoms selected from the group consisting of N, O and S, and wherein the heterocyclic or non-heterocyclic ring is unsubstituted or substituted with halogen or hydroxy, $C_{1-7}$ alkyl, unsubstituted or substituted with one or more of hydroxy, COOH, amino, aryl, $C_{3-7}$ cycloalkyl, $CF_3$, $N(CH_3)_2$, —$C_{1-3}$alkylaryl, heteroaryl, or heterocycloalkyl, $CF_3$, $C_{3-7}$ cycloalkyl, unsubstituted or substituted with aryl, $C_{7-12}$ bicyclic alkyl, or $C_{10-16}$ tricyclic alkyl;

$R^3$ is hydrogen, $C_{1-6}$ alkyl, $C_{3-7}$ cycloalkyl, $C_{2-6}$ alkenyl, $C_{2-6}$ alkynyl, optionally substituted $C_{6-10}$ aryl, optionally substituted $C_{6-10}$ ar($C_{1-6}$)alkyl, optionally substituted heteroaryl, trifluoromethyl, halogen, $C_{1-6}$ hydroxyalkyl, cyano, nitro, carboxamido, —$CO_2R^x$, —$CH_2O\ R^x$ or —$OR^x$, where $R^x$, in each instance, is independently one of hydrogen, $C_{1-6}$ alkyl or $C_{3-7}$ cycloalkyl wherein said alkyl or cycloalkyl groups may optionally have one or more unsaturations;

$R^4$ is hydrogen or halogen;

$R^{12}$ is hydrogen, phenyl, naphthyl, or biphenyl, each of which is unsubstituted or substituted with one or more of $C_{1-4}$ alkyl, $C_{1-4}$ alkoxy, halogen, hydroxy, $CF_3$, $OCF_3$, COOH, or $CONH_2$, a 5- to 7-membered mono- or a 9- to 10-membered bicyclic heterocyclic ring which can be saturated or unsaturated, and which contains from one to four heteroatoms selected from the group consisting of N, O and S, $C_{1-4}$ alkyl, unsubstituted or substituted with one or more of hydroxy, COOH, amino, aryl, heteroaryl, or heterocycloalkyl, $CF_3$, $C_{3-7}$ cycloalkyl, $C_{7-12}$ bicyclic alkyl, or $C_{10-16}$ tricyclic alkyl;

$R^5$ is hydrogen, $C_{1-4}$alkyl, or $C_{2-4}$ alkenyl;

A is one of

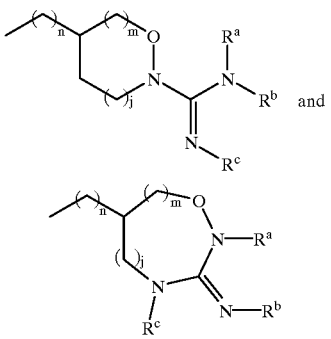

wherein:

$R^a$, $R^b$ and $R^c$ are independently hydrogen, alkyl, hydroxy, alkoxy, aryloxy, aralkoxy, alkoxycarbonyloxy, cyano or —$CO_2R^w$, where $R^w$ is alkyl, cycloalkyl, phenyl, benzyl,

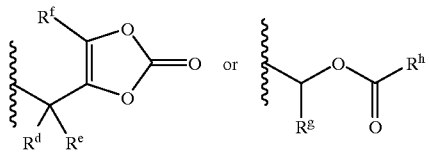

where $R^d$ and $R^1$ are independently hydrogen, $C_{1-6}$alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

each n is from zero to 4, preferably zero to 2;

each m is from zero to 4, preferably zero to 2; and each j is zero to 4, preferably zero to 2;

provided that n, m and j are not all zero.

In one class of compounds and pharmaceutically acceptable salts thereof, $R^3$ is hydrogen, $C_{1-4}$ alkyl, $C_{3-7}$ cycloalkyl, or $CF_3$; preferably $C_{1-4}$ alkyl, and n is from zero to 2; m is from zero to 2; and j is from zero to 2, provided that n, m and j are not all zero.

In a subclass of this class of compounds and pharmaceutically acceptable salts thereof, $R^4$ is hydrogen or halogen.

In a group of this subclass of compounds and pharmaceutically acceptable salts thereof, W is H or $R^1$.

In a subgroup of this group of compounds and pharmaceutically acceptable salts thereof, $R^1$ is $R^2$, $R^2(CH_2)_tC(R^{12})_2$, where t is 0–3, and each $R^{12}$ can be the same or different, $R^2C(R^{12})_2(CH_2)_t$, wherein t is 0–3, and each $R^{12}$ can be the same or different, wherein $(R^{12})_2$ can also form a ring with C represented by $C_{3-7}$ cycloalkyl, $R^2CH_2C(R^{12})_2(CH_2)_q$, wherein q is 0–2, and each $R^{12}$ can be the same or different, wherein $(R^{12})_2$ can also form a ring with C represented by $C_{3-7}$cycloalkyl, $(R^2)_2CH(CH_2)_r$, where r is 0–4 and each $R^2$ can be the same or different, and wherein $(R^2)_2$ can also form a ring with CH represented by $C_{3-7}$ cycloalkyl, $C_{7-12}$ bicylic alkyl, $C_{10-16}$ tricylic alkyl, or a 5- to 7-membered mono- or bicylic heterocyclic ring which can be saturated or unsaturated, and which contains from one to three heteroatoms selected from the group consisting of N, O and S, $R^2CF_2C(R^{12})_2(CH_2)_q$, wherein q is 0–2, and each $R^{12}$ can be the same or different, wherein $(R^{12})_2$ can also form a ring with C represented by $C_{3-7}$cycloalkyl, or $R^2O\ (CH_2)_p$, wherein p is 2–4;

$R^2$ is phenyl or naphthyl, each of which is unsubstituted or substituted with one or more of $C_{1-4}$ alkyl, $C_{1-4}$ alkoxy, halogen, hydroxy, $CF_3$, $OCF_3$, or $SO_2NH_2$, a 5- to 7-membered mono- or a 9- to 10-membered bicyclic heterocyclic ring or non-heterocyclic ring which can be saturated or unsaturated, wherein the heterocyclic ring contains from one to four heteroatoms selected from the group consisting of N, O and S, and wherein the heterocyclic or non-heterocyclic ring is unsubstituted or substituted with halogen or hydroxy, $C_{1-7}$ alkyl, unsubstituted or substituted with one or more of hydroxy, COOH, $C_{3-7}$ cycloalkyl, $CF_3$, $N(CH_3)_2$, —$C_{1-3}$alkylaryl, heteroaryl, or heterocycloalkyl, $CF_3$, or $C_{3-7}$ cycloalkyl, unsubstituted or substituted with aryl; and $R^{12}$ is hydrogen, or $C_{1-4}$ alkyl, unsubstituted or substituted with one or more of hydroxy, COOH, amino, aryl, heteroaryl, or heterocycloalkyl.

In a family of this subgroup of compounds and pharmaceutically acceptable salts thereof, $R^3$ is H, $CH_3$, or $CH_2CH_3$;

$R^4$ is H or chloro; and

W is $PhCH_2CH_2$, $(CH_3)_3C-$, $HOOCCH_2$, $CF_3CH_2$, $(CH_3)_2N(CH_2)_2$, $PhCH_2O(CH_2)_2$, $PhCH(CH_3)$, $PhCH_2CH(COOH)$, $CH_3(CH_2)_5$, $PhCH_2$, H, $CH_3(CH_2)_4$, $CH_3CH_2CH(CH_3)CH_2$, $(Ph)_2CHCH_2$, $PhCH_2CH(CH_3)$, $PhCH(CH_3)CH_2$, $(CH_3)_2CH$, $PhCH(OH)CH_2$, $PhC(CH_3)_2CH_2$, $(Ph)_2CHCH_2$, or

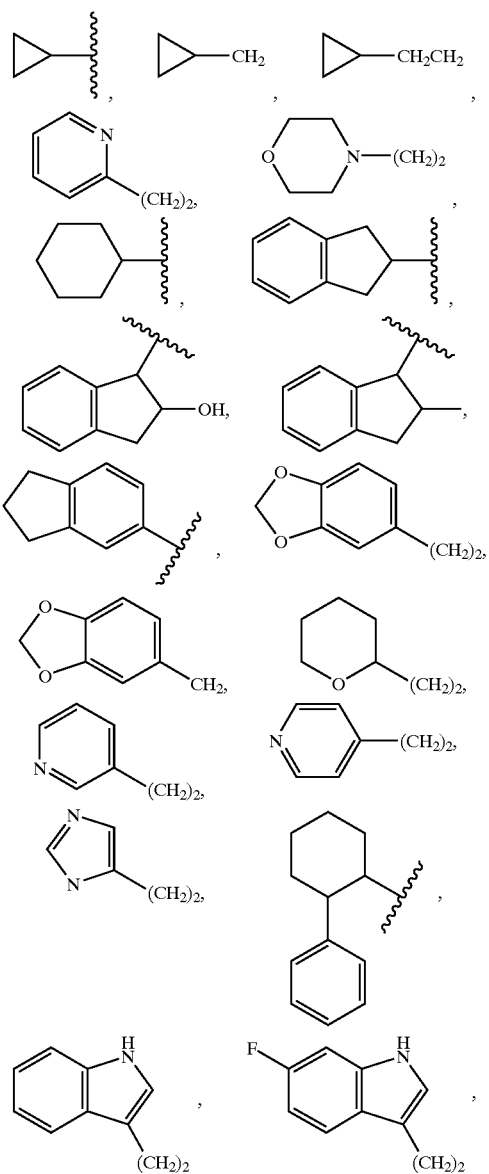

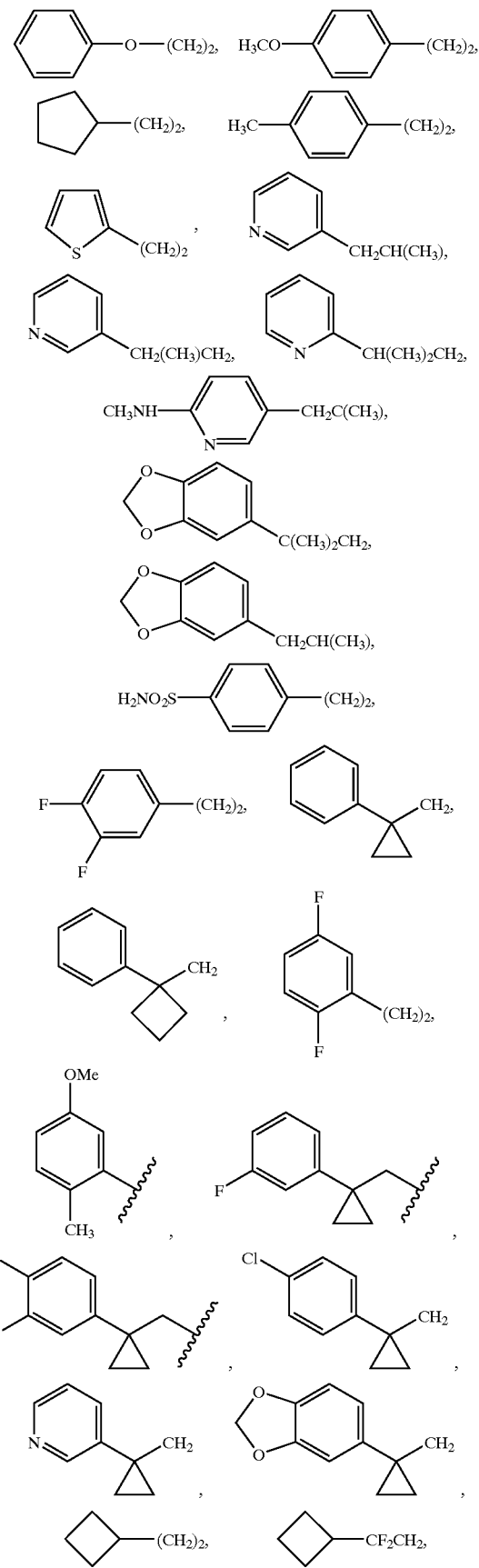

-continued

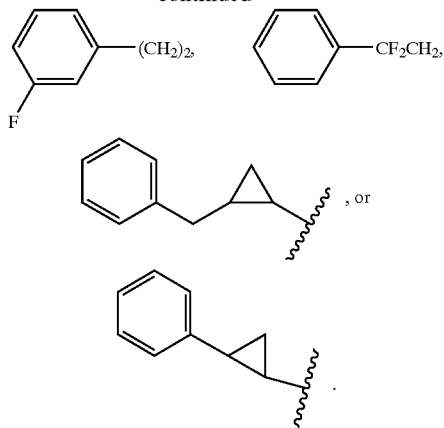

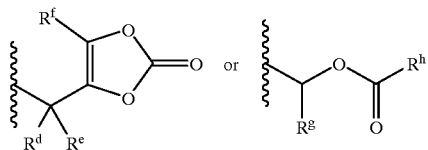

A preferred R⁵ group is hydrogen.

Preferred values of $R^a$, $R^b$ and $R^c$ in Formula I are hydrogen, hydroxy, $C_{1-6}$ alkyl, $C_{1-6}$ alkoxy, cyano or —$CO_2R^w$, where $R^w$, in each instance, is preferably one of $C_{1-4}$alkyl, $C_{4-7}$cycloalkyl or benzyloxycarbonyl. Suitable values of $R^a$, $R^b$ and $R^c$ include hydrogen, methyl, ethyl, propyl, n-butyl, hydroxy, methoxy, ethoxy, cyano, —$CO_2CH_3$, —$CO_2CH_2CH_3$ and —$CO_2CH_2CH_2CH_3$. In the most preferred embodiments, $R^a$, $R^b$ and $R^c$ are each hydrogen.

Also preferred at $R^a$, $R^b$ and $R^c$ is the group —$CO_2R^w$, where $R^w$ is one of

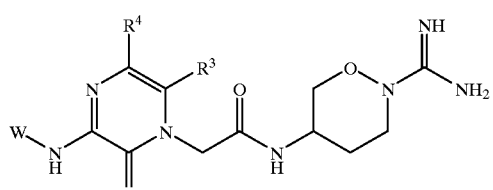

where $R^d$–$R^h$ are defined as above. When $R^a$, $R^b$ and $R^c$ are —$CO_2R^w$, where $R^w$ is one of these moieties, the resulting compounds are prodrugs that possess desirable formulation and bioavailability characteristics. A preferred value for each of $R^d$, $R^e$ and $R^g$ is hydrogen, $R^f$ is methyl, and preferred values for $R^h$ include benzyl and tert-butyl.

Preferred values of n in Formula I include zero, 1 or 2.

Preferred values of m are zero, 1 or 2.

Preferred values of j are zero, 1 or 2, provided that n, m and j are not all zero.

Especially preferred compounds are represented by Formulae Ia and Ib:

Ia

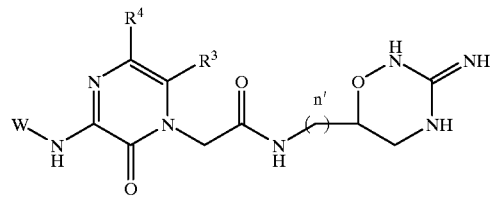

Ib

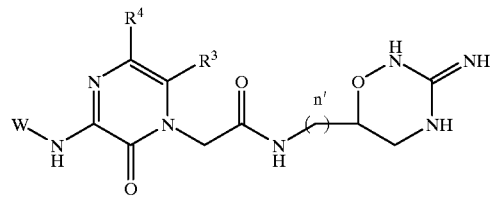

or a solvate, hydrate or pharmaceutically acceptable salt thereof; wherein

W is as defined, and has the preferred values, as for Formula I, above;

$R^3$ is hydrogen, $C_{1-3}$ alkyl, halogen or $C_{1-2}$ alkoxy;

$R^4$ is hydrogen or halogen; and n' is 0 or 1.

Specific compounds within the scope of the invention include the following:

N-(2-carbamimidoyl-[1,2]oxazinan-5-yl)-2-[6-methyl-2-oxo-3-(2-p-tolyl-ethylamino)-2H-pyrazin-1-yl]-acetamide;

2-[3-(2,2-difluoro-2-phenyl-ethylamino)-6-methyl-2-oxo-2H-pyrazin-1-yl]-N-(3-imino-[1,2,4]oxadiazinan-6-ylmethyl)-acetamide;

N-(2-carbamimidoyl-[1,2]oxazinan-5-yl)-2-(6-methyl-2-oxo-3-phenethylamino-2H-pyrazin-1-yl)-acetamide;

N-(2-carbamimidoyl-[1,2]oxazinan-5-yl)-2-(5-chloro-6-methyl-2-oxo-3-phenethylamino-2H-pyrazin-1-yl)-acetamide;

N-(2-carbamimidoyl-[1,2]oxazinan-5-yl)-2-[3-(2,2-diphenyl-ethylamino)-6-methyl-2-oxo-2H-pyrazin-1-yl]-acetamide;

N-(2-carbamimidoyl-[1,2]oxazinan-5-yl)-2-[5-chloro-3-(2,2-diphenyl-ethylamino)-6-methyl-2-oxo-2H-pyrazin-1-yl]-acetamide;

N-(2-carbamimidoyl-[1,2]oxazinan-5-yl)-2-{3-[2-(4-methoxy-phenyl)-ethylamino]-6-methyl-2-oxo-2H-pyrazin-1-yl}-acetamide;

N-(2-carbamimidoyl-[1,2]oxazinan-5-yl)-2-{6-methyl-2-oxo-3-[(1-phenyl-cyclobutylmethyl)-amino]-2H-pyrazin-1-yl}-acetamide;

N-(2-carbamimidoyl-[1,2]oxazinan-5-yl)-2-[6-methyl-3-(2-naphthalen-1-yl-ethylamino)-2-oxo-2H-pyrazin-1-yl]-acetamide;

N-(2-carbamimidoyl-[1,2]oxazinan-5-yl)-2-[6-methyl-2-oxo-3-(2-phenyl-butylamino)-2H-pyrazin-1-yl]-acetamide;

2-[3-(2-benzo[1,3]dioxol-5-yl-ethylamino)-6-methyl-2-oxo-2H-pyrazin-1-yl]-N-(2-carbamimidoyl-[1,2]oxazinan-5-yl)-acetamide;

N-(2-carbamimidoyl-[1,2]oxazinan-5-yl)-2-[6-methyl-2-oxo-3-(2-pyridin-2-yl-ethylamino)-2H-pyrazin-1-yl]-acetamide;

N-(2-carbamimidoyl-[1,2]oxazinan-5-yl)-2-[6-methyl-2-oxo-3-(2-o-tolyl-ethylamino)-2H-pyrazin-1-yl]-acetamide;

N-(2-carbamimidoyl-[1,2]oxazinan-5-yl)-2-[6-methyl-2-oxo-3-(2-m-tolyl-ethylamino)-2H-pyrazin-1-yl]-acetamide;

N-(2-carbamimidoyl-[1,2]oxazinan-5-yl)-2-{6-methyl-2-oxo-3-[2-(2-trifluoromethyl-phenyl)-ethylamino]-2H-pyrazin-1-yl}-acetamide;

N-(2-carbamimidoyl-[1,2]oxazinan-5-yl)-2-{6-methyl-2-oxo-3-[2-(3-trifluoromethyl-phenyl)-ethylamino]-2H-pyrazin-1-yl}-acetamide;

N-(2-carbamimidoyl-[1,2]oxazinan-5-yl)-2-{6-methyl-2-oxo-3-[2-(4-trifluoromethyl-phenyl)-ethylamino]-2H-pyrazin-1-yl}-acetamide;

N-(2-carbamimidoyl-[1,2]oxazinan-5-yl)-2-{3-[2-(3,5-dimethyl-phenyl)-ethylamino]-6-methyl-2-oxo-2H-pyrazin-1-yl}-acetamide;

N-(2-carbamimidoyl-[1,2]oxazinan-5-yl)-2-[3-(indan-2-ylamino)-6-methyl-2-oxo-2H-pyrazin-1-yl]-acetamide;

N-(2-carbamimidoyl-[1,2]oxazinan-5-yl)-2-{3-[2-(3,4-difluoro-phenyl)-ethylamino]-6-methyl-2-oxo-2H-pyrazin-1-yl}-acetamide;

N-(2-carbamimidoyl-[1,2]oxazinan-5-yl)-2-[3-(2-indan-5-yl-ethylamino)-6-methyl-2-oxo-2H-pyrazin-1-yl]-acetamide;

N-(2-carbamimidoyl-[1,2]oxazinan-5-yl)-2-{3-[2-(2-fluoro-phenyl)-ethylamino]-6-methyl-2-oxo-2H-pyrazin-1-yl}-acetamide;

N-(2-carbamimidoyl-[1,2]oxazinan-5-yl)-2-{3-[2-(3,4-dimethoxy-phenyl)-ethylamino]-6-methyl-2-oxo-2H-pyrazin-1-yl}-acetamide;

N-(2-carbamimidoyl-[1,2]oxazinan-5-yl)-2-{3-[2-(4-fluoro-phenyl)-ethylamino]-6-methyl-2-oxo-2H-pyrazin-1-yl}-acetamide;

N-(2-carbamimidoyl-[1,2]oxazinan-5-yl)-2-{3-[2-(4-ethyl-phenyl)-ethylamino]-6-methyl-2-oxo-2H-pyrazin-1-yl}-acetamide;

N-(2-carbamimidoyl-[1,2]oxazinan-5-yl)-2-[6-methyl-2-oxo-3-(2-phenyl-propylamino)-2H-pyrazin-1-yl]-acetamide;

N-(2-carbamimidoyl-[1,2]oxazinan-5-yl)-2-{3-[2-(3,4-dimethyl-phenyl)-ethylamino]-6-methyl-2-oxo-2H-pyrazin-1-yl}-acetamide;

N-(2-carbamimidoyl-[1,2]oxazinan-5-yl)-2-[6-methyl-3-(2-naphthalen-2-yl-ethylamino)-2-oxo-2H-pyrazin-1-yl]-acetamide;

N-(2-carbamimidoyl-[1,2]oxazinan-5-yl)-2-[3-(2,2-diphenyl-propylamino)-6-methyl-2-oxo-2H-pyrazin-1-yl]-acetamide;

N-(2-carbamimidoyl-[1,2]oxazinan-5-yl)-2-{3-[2-(1h-indol-3-yl)-ethylamino]-6-methyl-2-oxo-2H-pyrazin-1-yl}-acetamide;

N-(2-carbamimidoyl-[1,2]oxazinan-5-yl)-2-{6-methyl-3-[2-(4-methyl-naphthalen-1-yl)-ethylamino]-2-oxo-2H-pyrazin-1-yl}-acetamide;

N-(2-carbamimidoyl-[1,2]oxazinan-5-yl)-2-{3-[2-(2,4-difluoro-phenyl)-ethylamino]-6-methyl-2-oxo-2H-pyrazin-1-yl}-acetamide;

N-(2-carbamimidoyl-[1,2]oxazinan-5-yl)-2-[3-(2,2-difluoro-2-phenyl-ethylamino)-6-methyl-2-oxo-2H-pyrazin-1-yl]-acetamide;

N-(3-imino-[1,2,4]oxadiazinan-6-ylmethyl)-2-(6-methyl-2-oxo-3-phenethylamino-2H-pyrazin-1-yl)-acetamide;

2-(5-chloro-6-methyl-2-oxo-3-phenethylamino-2H-pyrazin-1-yl)-N-(3-imino-[1,2,4]oxadiazinan-6-ylmethyl)-acetamide;

2-[3-(2,2-diphenyl-ethylamino)-6-methyl-2-oxo-2H-pyrazin-1-yl]-N-(3-imino-[1,2,4]oxadiazinan-6-ylmethyl)-acetamide;

2-[5-chloro-3-(2,2-diphenyl-ethylamino)-6-methyl-2-oxo-2H-pyrazin-1-yl]-N-(3-imino-[1,2,4]oxadiazinan-6-ylmethyl)-acetamide;

N-(3-imino-[1,2,4]oxadiazinan-6-ylmethyl)-2-[6-methyl-2-oxo-3-(2-p-tolyl-ethylamino)-2H-pyrazin-1-yl]-acetamide;

N-(3-imino-[1,2,4]oxadiazinan-6-ylmethyl)-2-{3-[2-(4-methoxy-phenyl)-ethylamino]-6-methyl-2-oxo-2H-pyrazin-1-yl}-acetamide;

N-(3-imino-[1,2,4]oxadiazinan-6-ylmethyl)-2-{6-methyl-2-oxo-3-[(1-phenyl-cyclobutylmethyl)-amino]-2H-pyrazin-1-yl}-acetamide;

N-(3-imino-[1,2,4]oxadiazinan-6-ylmethyl)-2-[6-methyl-3-(2-naphthalen-1-yl-ethylamino)-2-oxo-2H-pyrazin-1-yl]-acetamide;

N-(3-imino-[1,2,4]oxadiazinan-6-ylmethyl)-2-[6-methyl-2-oxo-3-(2-phenyl-butylamino)-2H-pyrazin-1-yl]-acetamide;

2-[3-(2-benzo [1,3]dioxol-5-yl-ethylamino)-6-methyl-2-oxo-2H-pyrazin-1-yl]-N-(3-imino-[1,2,4]oxadiazinan-6-ylmethyl)-acetamide;

N-(3-imino-[1,2,4]oxadiazinan-6-ylmethyl)-2-[6-methyl-2-oxo-3-(2-pyridin-2-yl-ethylamino)-2H-pyrazin-1-yl]-acetamide;

N-(3-inino-[1,2,4]oxadiazinan-6-ylmethyl)-2-[6-methyl-2-oxo-3-(2-o-tolyl-ethylamino)-2H-pyrazin-1-yl]-acetamide;

N-(3-imino-[1,2,4]oxadiazinan-6-ylmethyl)-2-[6-methyl-2-oxo-3-(2-m-tolyl-ethylamino)-2H-pyrazin-1-yl]-acetamide;

N-(3-imino-[1,2,4]oxadiazinan-6-ylmethyl)-2-{6-methyl-2-oxo-3-[2-(2-trifluoromethyl-phenyl)-ethylamino]-2H-pyrazin-1-yl}-acetamide;

N-(3-imino-[1,2,4]oxadiazinan-6-ylmethyl)-2-{6-methyl-2-oxo-3-[2-(3-trifluoromethyl-phenyl)-ethylamino]-2H-pyrazin-1-yl}-acetamide;

N-(3-imino-[1,2,4]oxadiazinan-6-ylmethyl)-2-{6-methyl-2-oxo-3-[2-(4-trifluoromethyl-phenyl)-ethylamino]-2H-pyrazin-1-yl}-acetamide;

2-{3-[2-(3,5-dimethyl-phenyl)-ethylamino]-6-methyl-2-oxo-2H-pyrazin-1-yl}-N-(3-imino-[1,2,4]oxadiazinan-6-ylmethyl)-acetamide;

N-(3-imino-[1,2,4]oxadiazinan-6-ylmethyl)-2-[3-(indan-2-ylamino)-6-methyl-2-oxo-2H-pyrazin-1-yl]-acetamide;

2-{3-[2-(3,4-difluoro-phenyl)-ethylamino]-6-methyl-2-oxo-2H-pyrazin-1-yl}-N-(3-imino-[1,2,4]oxadiazinan-6-ylmethyl)-acetamide;

N-(3-imino-[1,2,4]oxadiazinan-6-ylmethyl)-2-[3-(2-indan-5-yl-ethylamino)-6-methyl-2-oxo-2H-pyrazin-1-yl]-acetamide;

2-{3-[2-(2-fluoro-phenyl)-ethylamino]-6-methyl-2-oxo-2H-pyrazin-1-yl}-N-(3-imino-[1,2,4]oxadiazinan-6-ylmethyl)-acetamide;

2-{3-[2-(3,4-dimethoxy-phenyl)-ethylamino]-6-methyl-2-oxo-2H-pyrazin-1-yl}-N-(3-imino-[1,2,4]oxadiazinan-6-ylmethyl)-acetamide;

2-{3-[2-(4-fluoro-phenyl)-ethylamino]-6-methyl-2-oxo-2H-pyrazin-1-yl}-N-(3-imino-[1,2,4]oxadiazinan-6-ylmethyl)-acetamide;

2-{3-[2-(4-ethyl-phenyl)-ethylamino]-6-methyl-2-oxo-2H-pyrazin-1-yl}-N-(3-imino-[1,2,4]oxadiazinan-6-ylmethyl)-acetamide;

N-(3-imino-[1,2,4]oxadiazinan-6-ylmethyl)-2-[6-methyl-2-oxo-3-(2-phenyl-propylamino)-2H-pyrazin-1-yl]-acetamide;

2-{3-[2-(3,4-dimethyl-phenyl)-ethylamino]-6-methyl-2-oxo-2H-pyrazin-1-yl }-N-(3-imino-[1,2,4]oxadiazinan-6-ylmethyl)-acetamide;

N-(3-imino-[1,2,4]oxadiazinan-6-ylmethyl)-2-[6-methyl-3-(2-naphthalen-2-yl-ethylamino)-2-oxo-2H-pyrazin-1-yl]-acetamide;

2-[3-(2,2-diphenyl-propylamino)-6-methyl-2-oxo-2H-pyrazin-1-yl]-N-(3-imino-[1,2,4]oxadiazinan-6-ylmethyl)-acetamide;

N-(3-imino-[1,2,4]oxadiazinan-6-ylmethyl)-2-{3-[2-(1H-indol-3-yl)-ethylamino]-6-methyl-2-oxo-2H-pyrazin-1-yl}-acetamide;

N-(3-imino-[1,2,4]oxadiazinan-6-ylmethyl)-2-{6-methyl-3-[2-(4-methyl-naphthalen-1-yl)-ethylamino]-2-oxo-2H-pyrazin-1-yl}-acetamide;

2-{3-[2-(2,4-difluoro-phenyl)-ethylamino]-6-methyl-2-oxo-2H-pyrazin-1-yl}-N-(3-imino-[1,2,4]oxadiazinan-6-ylmethyl)-acetamide;

N-(3-imino-[1,2,4]oxadiazinan-6-ylmethyl)-2-[6-methyl-2-oxo-3-(2-p-tolyl-ethylamino)-2H-pyrazin-1-yl]-acetamide; and 2-[3-(2,2-difluoro-2-phenyl-ethylamino)-6-methyl-2-oxo-2H-pyrazin-1-yl]-N-(3-imino-[1,2,4]oxadiazinan-6-ylmethyl)-acetamide, as well as pharmaceutically acceptable salts thereof, for example the hydrochloride, acetate and trifluoroacetate salts thereof.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series. The compounds of the present invention may also have polymorphic crystalline forms, with all polymorphic crystalline forms being included in the present invention.

The compounds of Formula I may also be solvated, especially hydrated. Hydration may occur during manufacturing of the compounds or compositions comprising the compounds, or the hydration may occur over time due to the hygroscopic nature of the compounds.

Certain compounds within the scope of Formula I are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process. Useful prodrugs are those where $R^a$, $R^b$ and/or $R^c$ are —CO$_2$R$^w$, where R$^w$ is defined above. See, U.S. Pat. No. 5,466,811 and Saulnier et al., Bioorg. Med. Chem. Lett. 4:1985–1990 (1994).

When any variable occurs more than one time in any constituent or in Formula I, its definition on each occurrence is independent of its definition at every other occurrence. Also, combinations of substituents and/or variables are permissible only if such combinations result in stable compounds.

In another aspect, the present invention includes compositions which are useful for in vivo imaging of thrombi in a mammal, comprising a compound of the present invention which is capable of being detected outside the body. Preferred are compositions comprising a compound of the present invention and a detectable label, such as a radioactive or paramagnetic atom.

In another aspect, the present invention provides diagnostic compositions which are used for in vivo imaging of thrombi in a mammal, comprising a pharmaceutically acceptable carrier and a diagnostically effective amount of a compound or composition of the present invention.

In another aspect, the present invention includes methods which are useful for in vivo imaging of thrombi in a mammal.

According to a preferred aspect, useful compounds are those wherein the $R^1$ substituent is substituted with a detectable label, such as a radioactive iodine atom, such as I-125, I-131 or I-123. In this aspect, $R^1$ is preferably phenyl, having a para I-123, para I-125 or para I-131 substitution, or benzyl, having a meta I-123, meta I-125 or meta I-131 substitution.

The detectable label can also be a radioactive or paramagnetic chelate in which a suitable ligand (L) is attached to an $R^1$ substituent, either directly or via a divalent linking group A". Alternatively, the group —A"—L substitutes for the groups W in Formula I. By suitable ligand is meant an organic moiety that is capable of chelating a radioactive or paramagnetic metal ion.

In these compounds, the divalent linking group A" includes groups that are capable of covalently bonding with a free amino group and the chelating means. For example, A" may be —C(=S)—, —C(=O)—, —C(=NH)—(CH$_2$)$_6$—C(=NH)—, —C(=O)—(CH$_2$)$_6$—C(=O)—,

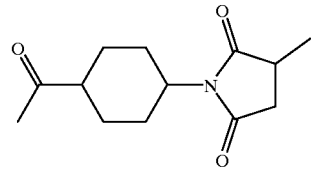

and the like.

Also, in the compounds represented by Formula I, the chelating ligand, L, includes groups capable of covalently bonding to or noncovalently binding to either a radioactive or paramagnetic atom. The chelating means including those which are customarily used for complexing radioactive or paramagnetic atoms. These include chelating means containing 3 to 12, preferably 3 to 8, methylene phosphonic acid groups, methylene carbohydroxamic acid groups, carboxyethylidene groups, or especially carboxymethylene groups, which are bonded to a nitrogen atom. If only one or two of the acid groups are bonded to a nitrogen atom, then that nitrogen is bonded to another nitrogen atom having such groups by an optionally substituted ethylene groups or by up to four separated ethylene units separated by a nitrogen or oxygen or sulfur atom. Preferred as a completing means is diethylenetrimine-N,N,N',N",N"-pentaacetic acid (DTPA). DTPA is well known in the art as a chelating means for the radioactive atom indium-111 (In-111), technetium-99m (Tc-99m), and the paramagnetic atom gadolinium (Gd). Khaw, et al., Science 209:295 (1980); Paik C. H. et al., U.S. Pat. No. 4,652,440 (1987); Gries, H. et al., U.S. Pat. No. 4,957,939 (1990). An preferred chelating ligand, L, is 1-(p-aminobenzyl)-diethylenetriaminepentaacetic acid. Also included as chelating means are compounds which contain sulfhydryl or amine moieties, the total of which in any combination is at least four. These sulfhydryl or amine moieties are separated from each other by at least two atoms which can be either carbon, nitrogen, oxygen, or sulfur. Especially preferred for chelating means, L, is metallothionein which is well known in the art as a chelating means for Tc-99m.

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2–20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "heteroaryl" as employed herein refers to groups having 5 to 14 ring atoms; 6, 10 or 14π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2, 3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms, preferably 3 to 7 carbon atoms. Typical examples are cyclopropyl, cyclobutyl, cyclopentyl, cyclohexyl, cycloheptyl, cyclooctyl and cyclononyl.

The term "$C_{7-12}$ bicyclic alkyl" is intended to include bicyclo[2.2.1]heptyl (norbornyl), bicyclo[2.2.2]octyl, 1,1, 3-trimethylbicyclo[2.2.1]heptyl (bornyl), and the like.

The term "$C_{10-16}$ tricyclic alkyl" is intended to include tricyclo[5, 2, 1, $0^{2,6}$] decyl, adamantyl, and the like.

The term "halogen" or "halo" as employed herein by itself or as part of another group refers to chlorine, bromine, fluorine or iodine with chlorine being preferred.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms.

The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "heterocycle" or "heterocyclic ring", as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "heteroatom" is used herein to mean an oxygen atom ("O"), a sulfur atom ("S") or a nitrogen atom ("N"). It will be recognized that when the heteroatom is nitrogen, it may form an $NR^a R^b$ moiety, wherein $R^a$ and $R^b$ are, independently from one another, hydrogen or $C_1$ to $C_8$ alkyl, or together with the nitrogen to which they are bound, form a saturated or unsaturated 5-, 6-, or 7-membered ring.

Schemes I, II, III, and IV outline the synthetic steps to produce compounds of Formula I. The schemes illustrate but are not limited to the preparation of the compounds of Examples 1 and 2.

In Schemes I, II, III, and IV, W, $R^3$, $R^a$, $R^b$, $R^c$, n, m, and j are as defined above; $R^4$=Cl or Br; P' is an ester protecting group, such as benzyl; $P^a$ and $P^c$ are amino protecting groups, such as benzyloxycarbonyl (Cbz) and tert-butoxycarbonyl (Boc); and $P^b$ is a hydroxyl protecting group, such as tetrahydropyranyl (THP), or 4-methoxyphenyl.

SCHEME I

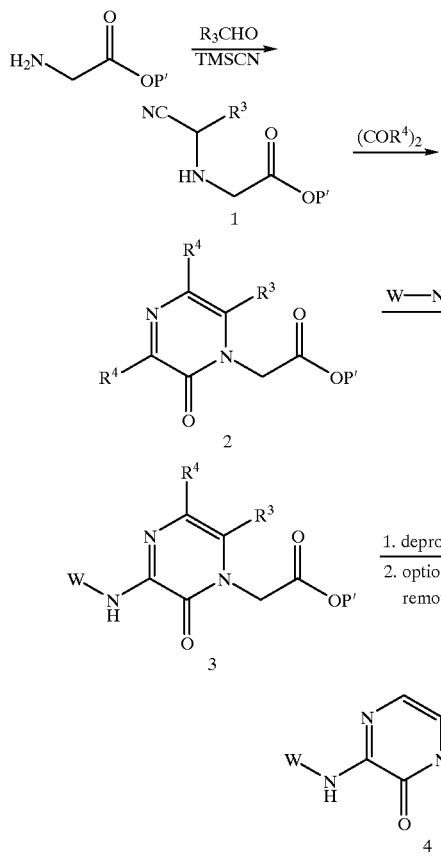

SCHEME II

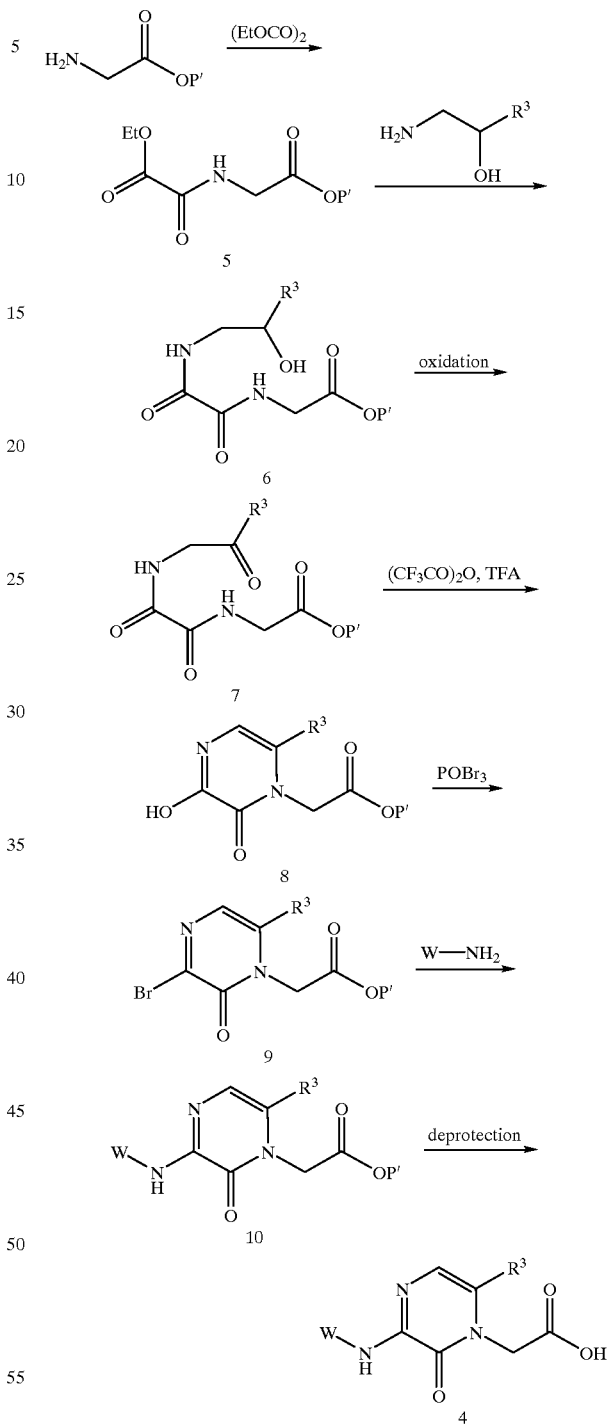

In Scheme I, an ester protected glycine, such as P'=benzyl or ethyl, is condensed with an aldehyde, such as acetaldehyde, and a cyanide, such as cyanotrimethylsilane (TMSCN), in a suitable solvent, such as dichloromethane to afford the aminonitrile 1. The aminonitrile is reacted with oxalyl chloride or oxalyl bromide in an appropriate solvent, such as 1,2-dichlorobenzene, to give the pyrazinone 2. The 3-chloro or 3-bromo of pyrazinone 2 is then displaced by an appropriate amine, such as phenethylamine, 2,2-diphenylethylamine or 4-methoxyphe nethylamine, in an appropriate solvent, such as ethyl acetate, to give compound 3. The ester 3 is converted to acid 4 by standard procedures well known in the art (Greene, T. W., Wuts, P. G. M., *Protective Groups in Organic Synthesis,* 2nd edition, John Wiley and Sons, Inc. New York (1991)), such as hydrolysis using a base, such as lithium hydroxide or sodium hydroxide, in a suitable solvent system, such as tetrahydrofuran/methanol/water. The 5-chlorine or bromine ($R^4$=Cl or Br) is then optionally reduced by hydrogenolysis using a catalyst, such as palladium on carbon or Raney nickel, in an appropriate solvent, such as water to afford 4. Alternatively, in the case of P'=benzyl, deprotection of the benzyl ester and removal of the 5-chlorine or bromine can be achieved simultaneously by hydrogenolysis to give 4.

Preparation of a number of useful intermediates according to this scheme is described in commonly assigned U.S. application Ser. No. 09/330,128, filed Jun. 11, 1999.

Alternatively, the pyrazinone scaffold could be prepared as shown in Scheme II. An ester protected glycine, such as P'=ethyl, or benzyl, is reacted with diethyl oxalate in a suitable solvent, such as ethanol, to give N-(ethyloxalyl) glycinate 5. Condensation of compound 5 with 1-amino-2-hydroxyalkane, such as 1-amino-2-propanol, in an appropriate solvent, such as ethanol, occurs to give 6. An oxidizing agent, such as ruthenium (III) chloride, oxidizes alcohol 6 to ketone 7 in an aqueous solution. Cyclization of 7 provides 3-hydroxypyrazinone 8 in the presence of trifluoroacetic anhydride in an acidic solvent, such as acetic acid. The 3-hydroxypyrazinone 8 is converted to 3-bromopyrazinone 9 by reacting with phosphorous oxybromide in a suitable solvent, such as chloroform. The 3-bromo in pyrazinone 9 is then displaced by an appropriate amine, such as phenethylamine or 2,2-difluorophenethylamine, in an appropriate solvent, such as toluene, at high temperature to give compound 10. Saponification of ester 10 to acid 4 is carried out by a standard procedure well known in the art. The preferred conditions include using an inorganic base, for example, lithium hydroxide or potassium hydroxide, in a suitable solvent system, such as methanol/tetrahydrofuran/water.

SCHEME III

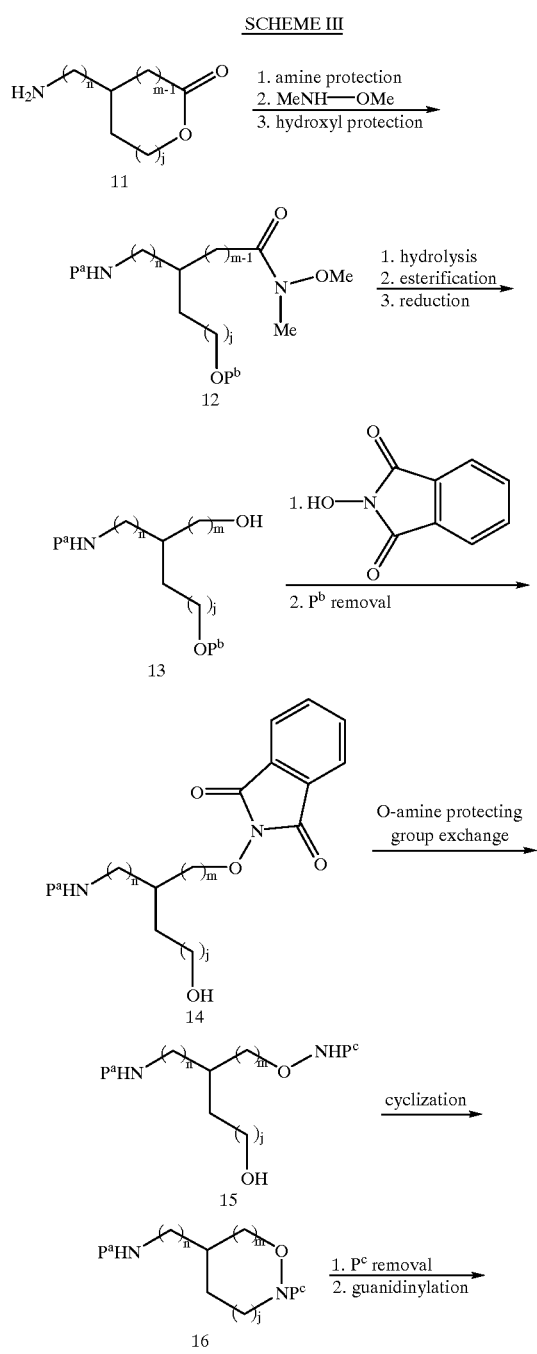

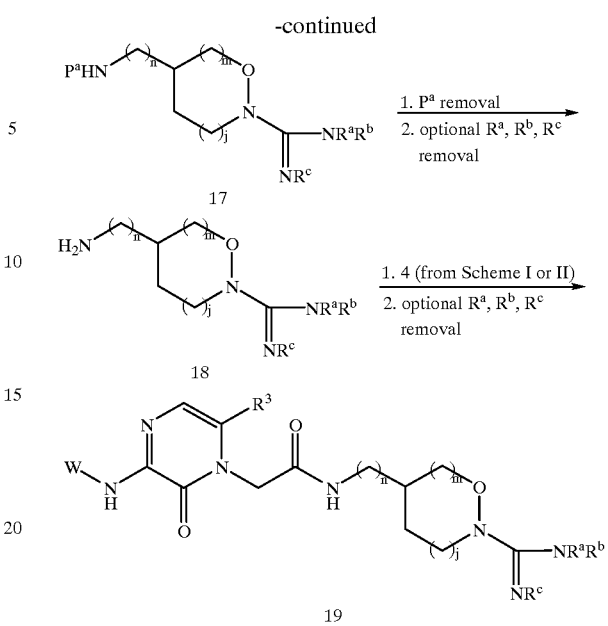

In Scheme III, aminolactone 11 is protected as benzylcarbamate under standard reaction conditions well known in the art. Aminolysis of the protected aminolactone effects in the presence of an amine, such as N,O-dimethylhydroxyamine, and a Lewis acid, such as aluminum chloride or trimethylaluminum, in a suitable solvent such as dichloromethane or 1,2-dichloroethane. The resulting hydroxy amide may be protected as an ether, for example, tetrahydropyranyl ether, under standard conditions.

Under standard conditions Weinreb amide 12 is converted to alcohol 13 stepwise. The sequence may include three steps: (1) hydrolysis of the amide 12 to a carboxylic acid in a basic alcoholic aqueous solution, (2) esterification of the acid to an alkyl carboxylic ester, and (3) reduction of the ester using an appropriate reducing agent, such as lithium borohydride. Alternatively, the amide 12 may be reduced to alcohol 13 in two steps employing suitable reducing agents. For example, amide 12 may be reduced with lithium aluminum hydride under carefully controlled conditions to an aldehyde, which is subsequently reduced to alcohol 13.

Under a standard Mitsunobu condition, alcohol 13 is reacted with N-hydroxyphthalimide. Removal of the hydroxyl protecting group $P^b$ to give compound 14 is accomplished by using a standard condition. For example, the tetrahydropyranyl ether may be removed by treatment with an acid, such as acetic acid, in a suitable aqueous solution, such as water and tetrahydrofuran. Exchanging of O-amine protecting group to secondary O-amine 15 is achieved by treatment of the phthalimide 14 with methylamine followed by protection of the released amine to carbamate 15, such as tert-butoxycarbamate, in a biphasic system composed of an organic solvent, such as dichloromethane, and a basic aqueous phase.

Under the standard Mitsunobu condition, intramolecular cyclization of 15 occurs to give cyclic compound 16. Preferred conditions include using a triarylphosphine, such as triphenylphosphine, and an azodicarbonyl reagent, such as diethyl azodicarboxylate, in a suitable solvent, such as tetrahydrofuran. Deprotection of the amino protecting group $P^c$ is routinely accomplished using the conventional conditions. For example, tert-butyloxycarbonyl (Boc) may be removed in acidic solutions, such as trifluoroacetic acid in dichloromethane. Guanidinylation of the resulting cyclic O-amine may be achieved employing a variety of guanidinylating reagents available, such as N,N'-bis(tert-butoxycarbonyl)-1H-pyrazole-1-carboxamidine.

Deprotection of the primary amine blocking group $P^a$ in 17 is routinely accomplished using conventional reaction conditions. For example, benzyloxycarbonyl protecting group may be removed by catalytic hydrogenation using palladium on carbon as a catalyst in a solvent, such as methanol or tetrahydrofuran. Alternatively, when $R^a$, $R^b$, and $R^c$ are tert-butyloxycarbonyl protecting groups, they can be optionally removed at the same time with the $p^a$ protecting group ($P^a$=Cbz). Strong acids, such as hydrobromic acid in acetic acid, may be used to effect this operation.

Amine 18 is coupled with pyrazinone acid 4 from Scheme I or II in the presence of a suitable coupling reagent and a base, such as Castro's reagent (BOP) and diisopropylethylamine, respectively, in a polar solvent, such as N,N-dimethylformamide. When $R^a$, $R^b$, and $R^c$ are protecting groups, for example, tert-butyloxycarbonyl, these groups can be optionally removed by treatment with an acid, usually trifluoroacetic acid, in a suitable solvent, such as dichloromethane.

SCHEME IV

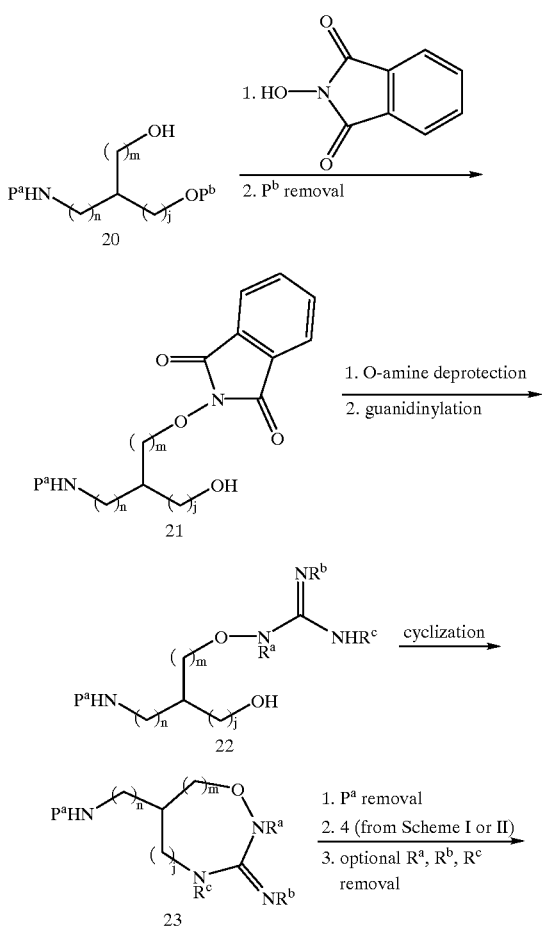

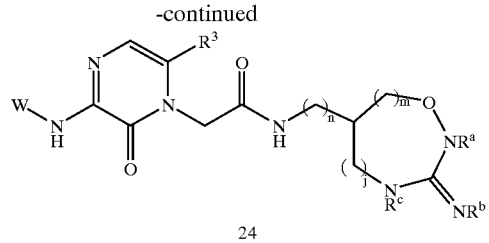

In Scheme IV, alcohol 20 is reacted with N-hydroxyphthalimide under Mitsunobu conditions. Preferred conditions include using a triarylphosphine, such as triphenylphosphine, and an azodicarbonyl reagent, such as diethyl azodicarboxylate, in a suitable solvent, such as tetrahydrofuran. Removal of the hydroxyl protecting group $P^b$ to give compound 21 is accomplished by using standard reaction conditions. The preferred condition for deprotection of 4-methoxyphenyl ether involves using ammonium cerium nitrate in a solvent mixture of acetonitrile and water.

Unblocking of the phthalimide protecting group is accomplished by employing a base, such as methylamine, in a suitable solvent, such as ethanol. Guanidinylation of the resulting alkoxyamine may be achieved by using a variety of guanidinylating reagents available, such as N,N'-bis(tert-butoxycarbonyl)-1H-pyrazole-1-carboxamidine. Intramolecular cyclization of 22 provides compound 23 under the standard Mitsunobu condition. Deprotection of the primary amine protecting group $P^a$ (Cbz) is routinely accomplished by catalytic hydrogenation using palladium on carbon as a catalyst in a suitable solvent, such as methanol or tetrahydrofuran. The resulting amine compound is coupled with acid 4 (from Scheme I or II) in the presence of a suitable coupling reagent and a base, such as Castro's reagent (BOP) and diisopropylethylamine, respectively, in a polar solvent, such as N,N-dimethylformamide. When $R^a$, $R^b$, and $R^c$ are protecting groups, for example, tert-butyloxycarbonyl (Boc), these groups can be optionally removed by treatment with an acid, usually trifluoroacetic acid, in a suitable solvent, such as dichloromethane.

The invention also relates to a process for preparing a cyclic oxyguanidine compound of the invention, comprising:

coupling or condensing a compound of formula:

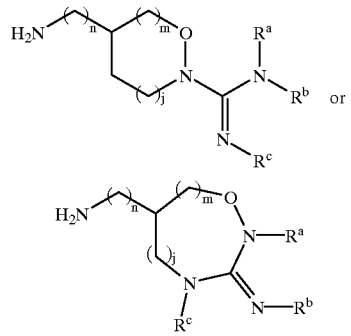

or a salt thereof, where $R^a$, $R^b$ and $R^c$ are as defined herein or optionally protected, and n, m and j are as defined herein, with a compound of Formula II:

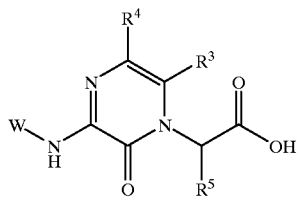

II where W, $R^3$, $R^4$, and $R^5$ are as defined herein. In general, protecting groups for the $R^a$, $R^b$, and $R^c$ groups may be employed where any one of $R^a$, $R^b$, and $R^c$ are hydrogen.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Preferred acids for forming acid addition salts include HCl and acetic acid.

The compounds of the present invention represent a novel class of potent inhibitors of metallo, acid, thiol and serine proteases. Examples of the serine proteases inhibited by compounds within the scope of the invention include leukocyte neutrophil elastase, a proteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coagulation pathway. Inhibition of thermolysin, a metalloprotease, and pepsin, an acid protease, are also contemplated uses of compounds of the present invention. The compounds of the present invention are preferably employed to inhibit trypsin-like proteases.

For their end-use application, the potency and other biochemical parameters of the enzyme-inhibiting characteristics of the compounds of the present invention is readily ascertained by standard biochemical techniques well known in the art. For example, an end use application of the compounds that inhibit chymotrypsin and trypsin is in the treatment of pancreatitis. Actual dose ranges for their specific end-use application will, of course, depend upon the nature and severity of the disease state of the patient or animal to be treated, as determined by the attending diagnostician. It is expected that a useful dose range will be about 0.01 to 10 mg per kg per day for an effective therapeutic effect.

Compounds of the present invention that are distinguished by their ability to inhibit thrombin may be employed for a number of therapeutic purposes. As thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; fibrin formation in the eye; hip replacement; and thrombus formation resulting from either thrombolytic therapy or percutaneous transluminal coronary angioplasty (PCTA). Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, and blood lines. The compounds of the present invention may also be used as an anticoagulant in extracorporeal blood circuits.

Metal stents have been shown to reduce restenosis, but are thrombogenic. A strategy for reducing the thrombogenicity of stents is to coat, embed, adsorb or covalently attach a thrombin-inhibiting agent to the stent surface. The compounds of the present invention can be employed for this purpose. Compounds of the invention can be attached to, or embedded within soluble and/or biodegradeable polymers as and thereafter coated onto stent materials. Such polymers can include polyvinylpyrrolidone, polyhydroxypropylmethacrylamide-phenol, polyhydroxyethylaspartamide-phenol, or polyethyleneoxide-polylysine substituted with palmitoyl residues, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. See European Application 761 251, European Application 604,022, Canadian Patent 2,164,684 and PCT Published Applications WO 96/11668, WO 96/32143 and WO 96/38136.

By virtue of the effects of thrombin on a host of cell types, such as smooth muscle cells, endothelial cells and neutrophils, the compounds of the present invention find additional use in the treatment or prophylaxis of adult respiratory distress syndrome; inflammatory responses; wound healing; reperfusion damage; atherosclerosis; and restenosis following an injury such as balloon angioplasty, atherectomy, and arterial stent placement.

The compounds of the present invention may be useful in treating neoplasia and metastasis as well as neurodegenerative diseases, such as Alzheimer's disease and Parkinson's disease.

When employed as thrombin inhibitors, the compounds of the present invention may be administered in an effective amount within the dosage range of about 0.1 to about 500 mg/kg, preferably between 0.1 to 10 mg/kg body weight, on a regimen in single or 2–4 divided daily doses.

When employed as inhibitors of thrombin, the compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

The thrombin inhibitors may also be coupled with soluble polymers as targetable drug carriers. Such polymers can include polyvinylpyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogens.

Human leucocyte elastase is released by polymorphonuclear leukocytes at sites of inflammation and thus is a contributing cause for a number of disease states. Compounds of the present invention are expected to have an anti-inflammatory effect useful in the treatment of gout, rheumatoid arthritis and other inflammatory diseases, and in the treatment of emphysema. The leucocyte elastase inhibitory properties of compounds of the present invention are determined by the method described below. Cathepsin G has also been implicated in the disease states of arthritis, gout and emphysema, and in addition, glomerulonephritis and lung infestations caused by infections in the lung. In their end-use application the enzyme inhibitory properties of the compounds of Formula I is readily ascertained by standard biochemical techniques that are well-known in the art.

The Cathepsin G inhibitory properties of compounds within the scope of the present invention are determined by the following method. A preparation of partially purified human Cathepsin G is obtained by the procedure of Baugh et al., *Biochemistry* 15:836 (1979). Leukocyte granules are a major source for the preparation of leukocyte elastase and cathepsin G (chymotrypsin-like activity). Leukocytes are lysed and granules are isolated. The leukocyte granules are extracted with 0.20 M sodium acetate, pH 4.0, and extracts are dialyzed against 0.05 M Tris buffer, pH 8.0 containing 0.05 M NaCl overnight at 4° C. A protein fraction precipitates during dialysis and is isolated by centrifugation. This fraction contains most of the chymotrypsin-like activity of leukocyte granules. Specific substrates are prepared for each enzyme, namely N—Suc-Ala-Ala-Pro-Val-p-nitroanilide and Suc-Ala-Ala-Pro-Phe-p-nitroanilide. The latter is not hydrolyzed by leukocyte elastase. Enzyme preparations are assayed in 2.00 mL of 0.10 M Hepes buffer, pH 7.5, containing 0.50 M NaCl, 10% dimethylsulfoxide and 0.0020 M Suc-Ala-Ala-Pro-Phe-p-nitroanilide as a substrate. Hydrolysis of the p-nitroanilide substrate is monitored at 405 nm and at 25° C.

Useful dose range for the application of compounds of the present invention as neutrophil elastase inhibitors and as Cathepsin G inhibitors depend upon the nature and severity of the disease state, as determined by the attending diagnostician, with a range of 0.01 to 10 mg/kg body weight, per day, being useful for the aforementioned disease states.

Compounds of the present invention that inhibit urokinase or plasminogen activator are potentially useful in treating excessive cell growth disease state. As such compounds of the present invention may also be useful in the treatment of benign prostatic hypertrophy and prostatic carcinoma, the treatment of psoriasis, and as abortifacients. For their end-use application, the potency and other biochemical parameters of the enzyme inhibiting characteristics of compounds of the present invention are readily ascertained by standard biochemical techniques well known in the art. Actual dose ranges for this application will depend upon the nature and severity of the disease state of the patient or animal to be treated as determined by the attending diagnostician. It is to be expected that a general dose range will be about 0.01 to 10 mg per kg per day for an effective therapeutic effect.

Additional uses for compounds of the present invention include analysis of commercial reagent enzymes for active site concentration. For example, chymotrypsin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent for quantitation of $\alpha_1$-antitrypsin in plasma. Plasma $\alpha_1$-antitrypsin increases in concentration during the course of several inflammatory diseases, and $\alpha_1$-antitrypsin deficiencies are associated with increased incidence of lung disease. Compounds of the present invention can be used to enhance the accuracy and reproducibility of these assays by titrametric standardization of the commercial elastase supplied as a reagent. See, U.S. Pat. No. 4,499,082.

Protease activity in certain protein extracts during purification of particular proteins is a recurring problem which can complicate and compromise the results of protein isolation procedures. Certain proteases present in such extracts can be inhibited during purification steps by compounds of the present invention, which bind tightly to various proteolytic enzymes.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in watersoluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

Compounds of Formula I can be labeled with radioactive iodine by using an exchange reaction. Exchange of hot iodine for cold iodine is well known in the art. Alternatively, a radio iodine labeled compound can be prepared from the corresponding bromo compound via a tributylstannyl intermediate. See, U.S. Pat. No. 5,122,361, herein incorporated by reference.

The present invention also includes compositions which are useful for in vivo imaging of thrombi in a mammal, wherein the compositions are comprised of a compound of Formula I complexed with a radioactive atom.

For the compounds of Formula I, suitable radioactive atoms include Co-57, Cu-67, Ga-67, Ga-68, Ru-97, Tc-99m, In-111, In-113m, Hg-197, Au-198, and Pb-203. Some radioactive atoms have superior properties for use in radiochemical imaging techniques. In particular, technetium-99m (Tc-99m) is an ideal radioactive atom for imaging because of its nuclear properties. It is a gamma emitter and has a single photon energy of 140 keV, a half-life of about 6 hours, and it is readily available from a Mo-99/Tc-99 generator. Rhenium-186 and -188 also have gamma emission which allows it to be imaged. Preferred compositions contain the radioactive atom, Tc-99m.

Compositions of the present invention are conveniently prepared by complexing a compound of Formula I with radioisotopes which are suitable for detection externally. The gamma emitters, indium-111m and technetium-99m, are preferred as radioactive atoms because they are detectable with a gamma camera and have favorable half-lives in vivo.

The compounds of Formula I can be labeled by any of the many techniques known in the art to provide a composition of the present invention. For example, these compounds can be labeled through a chelating agent such as diethylenetriaminepentaacetic acid (DTPA) or metallothionein, both of which can be covalently attached to the compound of Formula I.

In general, the compositions of the present invention containing technetium-99m are prepared by forming an aqueous mixture of technetium-99m and a reducing agent and a water-soluble ligand, and then contacting the mixture with a compound of the present invention represented by Formula I. For example, the imaging compounds of this invention are made by reacting technetium-99m (in an oxidized state) with the compounds of the present invention having a chelating means in the presence of a reducing agent to form a stable complex between technetium-99m in a reduced state (IV or V valence state).

One embodiment of the composition of the present invention is prepared by labeling a compound of Formula I having a DTPA chelating means with technetium-99m. This may be accomplished by combining a predetermined amount (as 5 $\mu$g to 0.5 mg) of compound of the present invention with an aqueous solution containing citrate buffer and stannous reducing agent, then adding freshly eluted sodium pertechnetate containing a predetermined level of radioactivity (as 15 mCi). After allowing an incubation of the mixture at room temperature, the reaction mixture is loaded into a shielded syringe through a sterile filter (0.2–0.22 micron), then is dispensed into 0.9% saline for injection, if desired.

Another embodiment of the compositions of the present invention is prepared by labeling a compound of Formula I having a metallothionein chelating means with technetium-99m. This may be accomplished by combining aqueous sodium pertechnetate-99m with aqueous stannous glucoheptonate to form a soluble complex of technetium-99m (in reduced state) with two glucoheptonate molecules, then combining this solution with a compound of the Formula I having a metallothionein attached thereto. After incubating the mixture for a period of time and under conditions which allow for an exchange of the technetium-99m from the glucoheptonate complex to the metallothionein of the compound of Formula I, the technetium-labeled composition of the present invention is formed.

The source of technetium-99m should preferably be water soluble. Preferred sources are alkali and alkaline earth metal pertechnetate ($TcO_4^-$). Technetium-99m is most preferably obtained in the form of fresh sodium pertechnetate from a sterile technetium-99m generator (as from a conventional Mo-99/Tc-99m generator). However, any other source of physiologically acceptable technetium-99m may be used.

Reducing agents for use in the method are physiologically acceptable for reducing technetium-99m from its oxidized state to the IV or V valence state or for reducing rhenium from its oxidized state. Reducing agents which can be used are stannous chloride, stannous fluoride, stannous glucoheptonate, stannous tartarate, and sodium dithionite. The preferred agents are stannous reducing agents, especially stannous chloride or stannous glucoheptonate. The amount of reducing agent is that amount necessary to reduce the technetium-99m to provide for the binding to the chelating means of a compound of Formula I in this radioisotope's reduced state. For example, stannous chloride ($SnCl_2$) is the reducing agent and can be used in range from 1–1,000 µg/mL. Especially preferred concentrations are about 30–500 pg/mL.

Citric acid complexes with technetium-99m quickly to form a stable technetium-99m-citrate complex. Upon contact with a compound of Formula I, substantially quantitative transfer of technetium-99m from its citrate complex to the chelating means of the compound of Formula I is achieved rapidly and under mild conditions. The amount of citric acid (as sodium citrate) can range from about 0.5 mg/ml up to the amount maximally soluble in the medium. Preferred amounts of citric acid range from 15 to 30 µg/ml.

The amount of compound of Formula I having a chelating means can range from 0.001 to about 3 mg/mL, preferably about 0.017 to about 0.15 mg/mL. Finally, technetium-99m in the form of pertechnetate can be used in amounts of preferably about 1–50 mCi. The amount of mCi per mg of compound of the present invention is preferably about 30–150.

The reaction between the compound of Formula I and the metal ion-transfer ligand complex is preferably carried out in a aqueous solution at a pH at which the compound of Formula I is stable. By "stable", it is meant that the compound remains soluble and retains its inhibitory activity against α-thrombin. Normally, the pH for the reaction will be from about 5 to 9, the preferred pH being above 6–8. The technetium-99m-citrate complex and a compound of Formula I are incubated, preferably at a temperature from about 20° C. to about 60° C., most preferably from about 20° C. to about 37° C., for a sufficient amount of time to allow transfer of the metal ion from the citrate complex to the chelating means of the compound of Formula I. Generally, less than one hour is sufficient to complete the transfer reaction under these conditions.

Alternative compositions of the present invention include an In-111 labeled compound of the present invention.

The present invention also includes compositions of the compounds of the present invention which are useful for in vivo imaging of thrombi in a mammal, comprised of a compound represented by Formula I complexed to a paramagnetic atom.

Preferred paramagnetic atoms are divalent or trivalent ions of elements with an atomic number of 21 to 29, 42, 44 and 58 to 70. Suitable ions include chromium(III), manganese(II), iron(III), iron(II), cobalt(II), nickel(II), copper(II), praseodymium(III), neodymium(III), samarium (III) and ytterbium(III). Because of their very strong magnetic moments, gadolinium(III), terbium(III), dysoprosium (III), holmium(III), and erbium(III) are preferred. Especially preferred for the paramagnetic atom is gadolinium(III).

The compositions of the present invention may be prepared by combining a compound of Formula I with a paramagnetic atom. For example, the metal oxide or a metal salt (for example, nitrate, chloride or sulfate) of a suitable paramagnetic atom is dissolved or suspended in a medium comprised of water and an alcohol, such as methyl, ethyl or isopropyl alcohol. This mixture is added to a solution of an equimolar amount of the compound of Formula I in a similar aqueous medium and stirred. The reaction mixture may be heated moderately until the reaction is completed. Insoluble compositions formed may be isolated by filtering, while soluble compositions may be isolated by evaporation of the solvent. If acid groups on the chelating means are still present in the composition of the present invention, inorganic or organic bases, and even amino acids, may be added to convert the acidic complex into a neutral complex to facilitate isolation or purification of homogenous composition. Organic bases or basic amino acids may be used as neutralizing agents, as well as inorganic bases such as hydroxides, carbonates or bicarbonates of sodium, potassium or lithium.

The present invention also include diagnostic compositions which are useful for in vivo imaging of thrombi in a mammal, comprising a pharmaceutically acceptable carrier and a diagnostically effective amount of compositions derived from the compounds of Formula I.

The "diagnostically effective amount" of the composition required as a dose will depend on the route of administration, the type of mammal being treated, and the physical characteristics of the specific mammal under consideration. These factors and their relationship to determining this dose are well known to skilled practitioners in the medial diagnostic arts. Also, the diagnostically effective amount and method of administration can be tailored to achieve optimal efficacy but will depend on such factors as weight, diet, concurrent medication and other factors which those skilled in the medical arts will recognize. In any regard, the dose for imaging should be sufficient for detecting the presence of the imaging agent at the site of a thrombus in question. Typically, radiologic imaging will require that the dose provided by the pharmaceutical composition position of the present invention be about 5 to 20 µCi, preferably about 10 µCi. Magnetic resonance imaging will require that the dose provided be about 0.001 to 5 mmole/kg, preferably about 0.005 to 0.5 mmole/kg of a compound of Formula I complexed with paramagnetic atom. In either case, it is known in the art that the actual dose will depend on the location of the thrombus.

"Pharmaceutically acceptable carriers" for in vivo use are well known in the pharmaceutical art, and are described, for example, in Remington's Pharmaceutical Sciences, Mack Publishing Co. (A. R. Gennaro edit. 1985). The pharmaceutical compositions of the present invention may be formulated with a pharmaceutically acceptable carrier to provide sterile solutions or suspensions for injectable administration. In particular, injectables can be prepared in conventional forms, either as liquid solutions or suspensions, solid forms suitable for solution or suspensions in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

The present invention also encompasses diagnostic compositions prepared for storage or administration. These would additionally contain preservatives, stabilizers and dyes. For example, sodium benzoate, sorbic acid and esters of p-hydroxybenzoic acid may be added as preservatives. Id. at 1449. In addition, antioxidants and suspending agents may be used.

The in vivo imaging methods of the present invention also offer several advantages over previous imaging techniques for the detection or monitoring of the presence, size, regression or increase of a thrombus. In particular, the present invention provides compounds, compositions and diagnostic compositions have been designed to bind extremely tightly to the thrombin associated with a thrombus and thereby reduce "background" due to circulating radioactivity or paramagnetism arising from unbound imaging agent. Furthermore, in vivo imaging by intracoronary injection of the compounds, compositions or diagnostic compositions of the present invention, is expected to be almost instantaneous since these imaging agents would saturate the thrombin bound to the thrombus immediately.

Accordingly, the present invention also includes methods for in vivo imaging of a thrombus in a mammal, comprising the steps of: (1) administering to a mammal a diagnostically acceptable amount of a compound, composition, or diagnostic composition of the present invention and (2) detecting a thrombus in a blood vessel.

The term "in vivo imaging" as used herein relates to methods of the detection of a thrombus in a mammal, as well as the monitoring of the size, location and number of thrombi in a mammal, as well as dissolution or growth of the thrombus.

In employing the compounds, compositions or diagnostic compositions in vivo by this method, "administering" is accomplished parenterally, in either a systemic or local targeted manner. Systemic administration is accomplished by injecting the compounds, compositions by diagnostic compositions of the present invention into a convenient and accessible vein or artery. This includes but is not limited to administration by the ankecubutal vein. Local targeted administration is accomplished by injecting the compounds, compositions or diagnostic compositions of the present invention proximal in flow to a vein or artery suspected to contain thrombi distal to the injection site. This includes but is not limited to direct injection into the coronary arterial vasculature to image coronary thrombi, into the carotid artery to image thrombi in the cerebral vasculature, or into a pedal vein to image deep vein thrombosis of the leg.

Also, the manner of delivery of a composition of the present invention to the site of a thrombus is considered within the scope of the term "administering". For example, a compound represented by Formula I having a chelating means attached thereto may be injected into the mammal, followed at a later time by the radioactive atom thereby forming in vivo at the site of the thrombus the composition comprising the compound of Formula I complexed to radioactive atom. Alternatively, a composition comprising the compound of Formula I complexed to radioactive atom may be injected into the mammal.

The "diagnostically effective amount" of the compounds, compositions or diagnostic compositions used in the methods of the present invention will, as previously mentioned, depend on the route of administration, the type of mammal being treated, and the physical characteristics of the specific mammal under treatment. These factors and their relationship to determining this dose are well known to skilled practitioners in the medical diagnostic arts. In any regard, the dose for in vivo imaging should be sufficient for detecting the presence of the imaging agent at the site of a thrombus in question. Typically, radiologic imaging will require that the dose provided by the diagnostic composition of the present invention be about 5 to 20 μCi, preferably about 10 μCi. Magnetic resonance imaging will require that the dose provided by the diagnostic composition be about 0.001 to 5 mmole/kg, preferably about 0.005 to 0.5 mmole/kg of a compound of Formula I complexed with paramagnetic atom. In either case, it is known in the art that the actual dose will depend on the location of the thrombus.

The detecting of a thrombus by imaging is made possible by the presence of radioactive or paramagnetic atoms localized at such thrombus.

The radioactive atoms associated with the compositions and diagnostic compositions of the present invention are preferably imaged using a radiation detection means capable of detecting gamma radiation, such as a gamma camera or the like. Typically, radiation imaging cameras employ a conversion medium (wherein the high energy gamma ray is absorbed, displacing an electron which emits a photon upon its return to the orbital state), photoelectric detectors arranged in a spatial detection chamber (to determine the position of the emitted photons), and circuitry to analyze the photons detected in the chamber and produce an image.

The paramagnetic atoms associated with the compositions and diagnostic compositions of the present invention are detected in magnetic resonance imaging (MRI) systems. In such systems, a strong magnetic field is used to align the nuclear spin vectors of the atoms in a patient's body. The field is disturbed by the presence of paramagnetic atoms localized at a thrombus and an image of the patient is read as the nuclei return to their equilibrium alignments.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLES

Example 1

N-(2-Carbamimidoyl-[1,2]oxazinan-5-yl)-2-[6-methyl-2-oxo-3-(2-p-tolylethyl-amino)-2H-pyrazin-1-yl]-acetamide trifluoroacetate

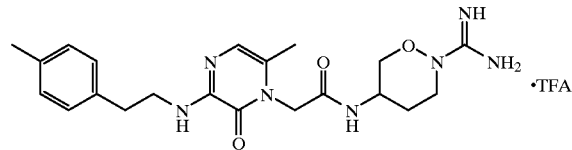

1. Benzyl-N-(1-cyanoethyl)glycine hydrochloride

Trimethylsilyl cyanide (4.0 mL, 30 mmol) was added cautiously to a stirred solution of benzyl glycine free base (5.0 g, 30 mmol) and acetaldehyde (1.7 mL, 30 mmol) in dichloromethane (15 mL) under argon atmosphere. After 15 hours, the volatile components were removed in vacuo, and the residue was dissolved in ethyl acetate (200 mL), washed with brine (100 mL), dried ($Na_2SO_4$) and evaporated to an oil. The oil was redissolved in ether (30 mL) and ethanol (30 mL), and 1 M HCl in ether (33 mL) was added dropwise to give the title compound as an off-white crystalline precipitate (6.60 g, 100%). mp: 137–138° C. $^1$H NMR ($CD_3OD$) δ 7.31–7.48 (m, 5H), 5.32 (s, 2H), 4.68 (q, 1H, J=7.0 Hz), 4.22 (s, 2H), 1.73 (d, 3H, J=7.1 Hz). CI MS m/z=192 (M+H). Anal. Calcd. for $C_{12}H_{14}N_2O_2 \cdot HCl$: C, 56.49; H, 5.95; N, 11.00. Found: C, 56.32; H, 5.88; N, 10.89.

2. 1-Benzyloxycarbonylmethyl-3,5-dichloro-6-methylpyrazinone

A stirred mixture of oxalyl chloride (5.3 mL, 60 mmol) and benzyl-N-(1-cyanoethyl)glycine hydrochloride (3.82 g, 15 mmol), as prepared in the preceding step, in 1,2-dichlorobenzene (30 mL) was heated to 100° C. overnight. The solvent was evaporated in vacuo and the residue was purified by flash column chromatography to give a solid. 10% Ethyl acetate in hexane (100 mL) was added and the solid was collected to give the title compound as an orange crystalline solid (2.7 g, 55%). $^1$H NMR (CDCl$_3$) δ 7.38 (m, 5H), 5.24 (s, 2H), 4.89 (s, 2H), 2.34 (s,3H).

3. 3-(2-4-Tolylethylamino)-5-chloro-6-methyl-1-(benzyloxycarbonylmethyl) pyrazinone A solution of 1-benzyloxycarbonylmethyl-3,5-dichloro-6-methylpyrazinone (656 mg, 2.00 mmol), as prepared in the preceding step, 4-methylphenethylamine (380 mg, 2.81 mmol), triethylamine (405 mg, 4.01 mmol), and ethyl acetate (20 mL) was refluxed overnight. After cooling to room temperature, the solution was washed with 10% citric acid (×2). The aqueous solutions were back extracted with dichloromethane. The combined organic layers were dried (Na$_2$SO$_4$) and contracted to give the title compound as a yellow solid (854 mg, 100%). $^1$H NMR (CDCl$_3$) δ 7.38–7.32 (m, 5H), 7.12 (s, 4H), 6.09 (s, 1H), 5.21 (s, 2H), 4.79 (s, 2H), 3.65 (dd, 2H, J=7.0, 13.0 Hz), 2.88 (t, 2H, J=7.1 Hz), 2.32 (s, 3H), 2.21 (s, 3H).

4. 3-(2-4-Tolylethylamino)-6-methyl-1-(carboxymethyl) pyrazinone

A mixture of 3-(2-4-tolylethylamino)-5-chloro-6-methyl-1-(benzyloxycarbonylmethyl)pyrazinone (854 mg, 2.00 mmol), as prepared in the preceding step, potassium hydroxide (452 mg, 8.00 mmol), 10% palladium on carbon (254 mg) in tetrahydrofuran (20 mL), methanol (30 mL), and water (7 mL) was stirred under hydrogen balloon for three days. The mixture was filtered through Celite. The filtrate was adjusted to pH 2–4 with 10% HCl and concentrated to about 2 mL under reduced pressure. The white solid which precipitated from the solution was filtered, washed with a small amount of water, and dried to give the title compound (137 mg, 22.7%). $^1$H NMR (CDCl$_3$) δ 7.20 (d, 2H, J=7.5 Hz), 7.10 (d, 2H, J=7.8 Hz), 6.70 (s, H), 4.71 (s, 2H), 2.87 (m, 2H), 2.50 (m, 2H), 2.26 (s, 3H), 2.15 (s, 3H).

5. N-(2-Oxo(3-3,4,5-trihydrofuryl))(phenylmethoxy) carboxamide

To a rapidly stirred mixture of α-amino-γ-butyrolactone hydrobromide (6.06 g, 33.3 mmol), sodium bicarbonate (14.0 g, 167 mmol), dichloromethane (50 mL), and water (50 mL) was added a solution of benzyl chloroformate (7.0 mL, 46.6 mmol) in dichloromethane (20 mL) dropwise via an additional funnel at room temperature. The solution was stirred overnight and then filtered. The filtrate was separated and the aqueous layer was extracted with dichloromethane. The combined organic layers were dried (Na$_2$SO$_4$), concentrated, and flash chromatographed to provide the title compound as a white solid (7.33 g, 93.7%). $^1$H NMR (CDCl$_3$) δ 7.41–7.31 (m, 5H), 5.32 (s(br), 1H), 5.14 (s, 2H), 4.49–4.37 (m, 2H) 4.30–4.22 (m, 1H), 2.84–2.76 (m, 1H), 2.29–2.14 (m, 1H).

6. 4-Hydroxy-N-methoxy-N-methyl-2-[(phenylmethoxy) carbonylamino]butanamide

To a suspension of aluminum chloride (4.30 g, 32.3 mmol) in anhydrous dichloromethane (200 mL) at 4° C. was added triethylamine (6.52 g, 64.6 mmol) in about 10 minutes. After completion of the addition, the cooling bath was removed and the homogeneous solution was stirred for 15 minutes. The product (5.06 g, 21.5 mmol) of the preceding step and N,O-dimethyl hydroxyamine hydrochloride (2.52 g, 25.8 mmol) were added at room temperature. After stirring for 5 hours, the reaction was quenched with water dropwise at 4° C. and stirring was continued for another 0.5 hours. The mixture was filtered, the filtrate was separated, and the aqueous layer was extracted with dichloromethane. The combined organic phases were washed with water, dried (Na$_2$SO$_4$), concentrated, and flash chromatographed to give the title compound as a clear oil (5.93 g, 93.0%). $^1$H NMR (CDCl$_3$) δ 7.37–7.32 (m, 5H), 5.83 (d, 1H, J=8.0 Hz), 5.12 (d, 2H, J=4.3 Hz), 4.87 (m, 1H), 3.78 (s, 3H), 3.73–3.65 (m, 2H), 3.22 (s, 3H), 3.11 (t, 1H, J=6.6 Hz), 2.10–2.05 (m, 1H), 1.65–1.55 (m, 1H).

7. N-methoxy-N-methyl-4-perhydro-2H-pyran-2-yloxy-2-[(phenylmethoxy) carbonylamino]butanamide A solution of the product (2.43 g, 8.21 mmol) of the preceding step, 3,4-dihydro-2H-pyran (2.07 g, 24.6 mmol), and pyridinium p-toluenesulfonate (200 mg, 0.796 mmol) in dichloromethane (50 mL) was stirred at room temperature overnight. Water was added and the aqueous layer was extracted with dichloromethane. The combined organic phases were dried (Na$_2$SO$_4$) and concentrated to give the title compound as a yellow oil (3.00 g, 96.2%). $^1$H NMR (CDCl$_3$) δ 7.37–7.30 (m, 5H), 5.76 (t, 1H, J=8.1 Hz), 5.16–5.03 (m, 2H), 4.85–4.81 (m, 1H), 4.58 (s, 1H), 3.89–3.81 (m, 1H), 3.79 (s, 3H), 3.51–3.40 (m, 2H), 3.22 (s, 3H), 2.25–1.50 (m, 9H).

8. N-[2-Hydroxy-1-(2-perhydro-2H-pyran-2-yloxyethyl)ethyl]-(phenylmethoxy)carboxamide The product (2.86 g, 7.53 mmol) of the preceding step in ethyl alcohol (60 mL) and water (15 mL) was treated with potassium hydroxide (1.69 g, 30.2 mmol) at room temperature overnight. After removal of ethyl alcohol under reduced pressure, the residue was diluted with dichloromethane and acidified to pH ~3 with 10% hydrochloric acid. The organic layer was separated and the aqueous layer was extracted with dichloromethane. A yellow oil (2.36 g, 93.0%) was obtained after drying and removal of dichloromethane in vacuo. To this oil (2.36 g, 7.00 mmol) in acetone (100 mL) was added potassium carbonate (1.94 g, 14.1 mmol) and iodomethane (1.30 mL, 20.9 mmol). The reaction mixture was heated at 60° C. overnight and filtered. The filtrate was concentrated and the residue was partitioned between dichloromethane and water. Drying and evaporation of solvent produced a yellow oil (2.30 g, 93.6%), which was diluted with tetrahydrofuran (30 mL) and treated with 2.0 M lithium borohydride (4.0 mL, 8.0 mmol) for 2.5 hours at room temperature. The reaction was quenched with a few drops of water. Brine and dichloromethane work-up, drying and removal of solvents yielded the title compound as a yellow oil (2.00 g, 94.5%). $^1$H NMR (CDCl$_3$) δ 7.38–7.29 (m,5H), 5.47 (m, 1H), 5.10 (s, 2H), 4.59–4.52 (m, 1H), 3.92–3.65 (m, 5H), 3.53–3.46 (m, 2H), 2.99–2.94 (m, 1H), 1.98–1.49 (m, 8H).

9. N-{1-[(1,3-Dioxoisoindolin-2-yloxy)methyl]-3-perhydro-2H-pyran-2-yl-oxypropyl}(phenylmethoxy)carboxamide To a solution of the product (2.00 g, 6.19 mmol), as prepared in the preceding step, triphenylphosphine (2.23 g, 8.51 mmol), N-hydroxyphthalimide (1.28 g, 7.85 mmol) and tetrahydrofuran (100 mL) was added diethyl azodicarboxylate (1.5 mL, 9.53 mmol). After stirring at room temperature overnight, the reaction solution was concentrated and flash chromatographed (SiO$_2$) to give the title compound as a yellow oil (2.84 g, 98.0%). $^1$H NMR (CDCl$_3$) δ 7.85–7.81 (m, 2H), 7.79–7.74 (m, 2H), 7.35–7.29 (m, 5H), 6.45 (s(br), 2H), 5.77–5.75 (m, 1H), 5.11–5.09 (m, 2H), 4.61–4.58 (m, 1H), 4.45–4.40 (m, 1H), 4.16–4.08 (m, 1H), 4.00–3.78 (m, 2H), 3.62–3.46 (m, 2H), 2.13–2.07 (m, 2H), 1.78–1.47 (m, 6H).

10. N-{1-[(1,3-Dioxoisoindolin-2-yloxy)methyl]-3-hydroxypropyl}-(phenylmethoxy)carboxamide A solution containing the product of the preceding step (290 mg, 0.620 mmol) in acetic acid (8 mL), tetrahydrofuran (4 mL) and water (2 mL) was heated at 55° C. for 3 hours. After concentration, flash chromatography of the residue provided the title compound as a white solid (225 mg, 94.6%). $^1$H NMR (CDCl$_3$) δ 7.87–7.84 (m, 2H), 7.79–7.76 (m, 2H), 7.39–7.35 (m, 5H), 6.00–5.98 (m, 1H), 5.20 (d, 1H, J=12.3 Hz), 5.11 (d, 1H, J=12.3 Hz), 4.45 (dd, 1H, J=4.0, 9.8 Hz), 4.26–4.14 (m, 2H), 3.80–3.70 (m, 2H), 3.08–3.04 (m, 1H), 2.02–1.79 (m, 2H).

11. N-(1-{[(tert-Butoxy)carbonylaminooxy]methyl}-3-hydroxypropyl)-(phenylmethoxy)carboxamide A solution of the product (4.10 g, 10.7 mmol), as prepared in the preceding step, tetrahydrofuran (40 mL), and methanol (40 mL) was treated with 40 wt. % methylamine in water (10 mL, 116 mmol) at room temperature for 1.5 hours. The solvents were evaporated, and a white solid was filtered and washed with diethyl ether. The filtrate was concentrated to a yellow oil. To a solution of the yellow oil, sodium bicarbonate (1.80 g, 21.4 mmol), dichloromethane (40 mL) and water (30 mL) was added dropwise a solution of di-tert-butyldicarbonate (3.00 g, 13.7 mmol) in dichloromethane (8 mL). After overnight at room temperature, the organic phase was separated and the aqueous phase was extracted with dichloromethane. The organic layer was dried, concentrated, and flash chromatographed to provide the title compound as a white semi-solid (3.20 g, 84.7%, 2 steps). $^1$H NMR (CDCl$_3$) δ 7.44 (s, 1H), 7.37–7.30 (m, 5H), 5.79 (d, 1 H, J=7.7 Hz), 5.13 (d, 2H, J=3.1 Hz), 4.13–4.06 (m, 1H), 3.98–3.89 (m, 2H), 3.70 (m, 2H), 1.85–1.78 (m, 1H), 1.70–1.62 (m, 1H), 1.47 (s, 9H).

12. tert-Butyl 5-[(phenylmethoxy)carbonylamino]-1,2-oxazaperhydroine-2-carboxylate To a solution of the product (3.20 g, 9.04 mmol) of the preceding step, triphenylphosphine (5.21 g, 19.9 mmol) and tetrahydrofuran (120 mL) was added diethyl azodicarboxylate (3.2 mL, 20.3 mmol) at 4° C. After stirring at 4° C. to room temperature for 3 hours, the solvent was evaporated and the residue was flash chromatographed to give the title compound as a yellow oil (2.50 g, 82.3%). $^1$H NMR (CDCl$_3$) δ 7.40–7.30 (m, 5H), 5.10 (s, 3H), 4.16–4.08 (m, 1H), 3.93 (m, 1H), 3.75–3.63 (m, 3H), 2.01–1.91 (m, 1H), 1.70–1.64 (m, 1H), 1.49 (s, 9H). Mass spectrum (LCMS, ESI) calcd. for C$_{17}$H$_{24}$N$_2$O$_5$: 359 (M+Na). Found: 359.

13. N-(1,2-Oxazaperhydroin-5-yl)(phenylmethoxy)carboxamide

A solution of the product (2.30 g, 6.85 mmol) of the preceding step in trifluoroacetic acid (10 mL) and dichloromethane (30 mL) was stirred at room temperature for 1.5 hours. After concentration in vacuo, the residue was partitioned between dichloromethane and saturated sodium bicarbonate. The organic phase was dried, concentrated, and flash chromatographed to give the title compound as a white solid (1.01 g, 62.5%). $^1$H NMR (CDCl$_3$) δ 7.37–7.32 (m, 5H), 5.10 (s, 2H), 5.05–5.01 (m, 1H), 4.07 (dd, 1H, J=3.1, 11.4 Hz), 3.84 (m, 1H), 3.62 (dd, 1 H, J=5.5, 11.3 Hz), 3.30–3.22 (m, 1H), 3.12–3.04 (m, 1H), 2.05–1.98 (m, 1H), 1.71–1.64 (m, 1H).

14. tert-Butyl-2-aza-3-[(tert-butoxy)carbonylamino]-3-{5-[(phenylmethoxy)-carbonylamino](1,2-oxazaperhydroin-2-yl)} prop-2-enoate The product (1.01 g, 4.28 mmol ) of the preceding step in N,N-dimethylformamide (60 mL) was reacted with N,N'-bis(tert-butoxycarbonyl)-1H-pyrazole-1-carboxamidine (1.60 g, 5.16 mmol) at 45° C. overnight. The solvent was evaporated and the residue was flash chromatographed to yield the title compound as a clear oil (1.90 g, 92.9%). $^1$H NMR (CDCl$_3$) δ 9.19 (s(br), 1H), 7.62 (d, 1H, J=2.1 Hz), 7.40–7.30 (m, 5H), 5.10 (s, 2H), 5.03 (d, 1H, J=7.6 Hz), 4.24 (dd, 1H, J=2.9, 11.3 Hz), 3.95 (m, 1H), 3.86–3.80 (m,3H), 2.11–2.01 (m,1H), 1.81–1.70 (m, 1H), 1.51 (s,9H), 1.49 (s, 9H). Mass spectrum (LCMS, ESI) calcd. for C$_{23}$H$_{34}$N$_4$O$_7$: 479 (M+H). Found: 479.

15. 5-Amino-1,2-oxazaperhydroine-2-carboxamidine hydrobromide

The product (1.88 g, 3.93 mmol) of the preceding step was treated with 30 wt. % hydrobromic acid in acetic acid (60 mL) at room temperature for 3.5 hours. After the reaction solution was concentrated under reduced pressure, a mixture of solvents including methanol, dichloromethane and hexane was added, and the solution was evaporated again to provide the title compound as a brown solid (1.41 g, 100%). $^1$H NMR (DMSO-d$_6$) δ 8.31 (s, 3H), 7.87 (s, 5H), 4.21 (dd, 1H, J=3.3, 12.0 Hz), 4.06–3.95 (m, 2H), 3.82–3.76 (m, 1H), 3.56–3.54 (m, 1H), 2.14–2.08 (m, 1H), 1.85–1.80 (m, 1H). Mass spectrum (LCMS, ESI) calcd. for C$_5$H$_{12}$N$_4$O: 145 (M+H). Found: 145.

16. N-(2-{[(tert-butoxy)carbonylamino]iminomethyl}(1,2-oxazaperhydroin-5-yl))-2-(6-methyl-3-{[2-(4-methylphenyl)ethyl]amino}-2-oxohydro-pyrazinyl)acetamide To a solution of 5-amino-1,2-oxazaperhydroine-2-carboxamidine hydrobromide (66 mg, 0.22 mmol), as prepared in the preceding step, and 3-(2-4-tolylethylamino)-6-methyl-1-(carboxymethyl)pyrazinone (80 mg, 0.27 mmol), as prepared in step 4 of Example 1, in N,N-dimethylformamide (5 mL) was added N,N-diisopropylethylamine (160 mg, 1.24 mmol) and Castro's reagent (100 mg, 0.226 mmol) at 4° C. After the solution was stirred at 4° C. to room temperature overnight, di-tert-butyldicarbonate (90 mg, 0.41 mmol) was added. After 6 hours, the solution was concentrated and the residue was partitioned between dichloromethane and 10% citric acid (×2). The aqueous layer was basified with potassium hydroxide and concentrated. To the residue was added dichloromethane, the resulting slurry was stirred for about one hour and then filtered. The filtrate was concentrated and flash chromatographed to give the pure title compound as a white solid (12 mg, 8.6%). The organic layer was dried, concentrated, and flash chromatographed to produce the title compound (13 mg, 9.3%). $^1$H NMR (CDCl$_3$) δ 7.14 (s, 4H), 6.98 (d, 1H, J=7.1 Hz), 6.77 (s, 1H), 5.92 (t, 1H, J=5.8 Hz), 4.57 (d, 2H, J=3.8 Hz), 4.15–4.09 (m, 2H), 3.86 (m, 2H), 3.78–3.74 (m, 1H), 3.62 (dd, 2H, J=6.9, 13.2 Hz), 2.89 (t, 2H, J=7.1 Hz), 2.25 (s, 3H), 2.12 (s, 3H), 2.01–1.96 (m, 1H), 1.73–1.67 (m, 1H), 1.47 (s, 9H).

17. N-(2-Carbamimidoyl-[1,2]oxazinan-5-yl)-2-[6-methyl-2-oxo-3-(2-p-tolyl-ethylamino)-2H-pyrazin-1-yl]-acetamide trifluoroacetate A solution of the product (12 mg, 0.023 mmol) of the preceding step in trifluoroacetic acid (0.5 niL) and dichloromethane (1 niL) was stirred at room temperature for 1 hours. The solution was concentrated to provide the title compound (13 mg, 100%). $^1$H NMR (DMSO-d$_6$) δ 8.56 (d, 1H, J=7.2 Hz), 7.94 (s, 4H), 7.10 (m, 4H), 6.67 (s, 1H), 4.62 (s, 2H), 4.08–3.92 (m, 3H), 3.74–3.67 (m, 2H), 3.53–3.48 (m, 2H), 2.82 (t, 2H, J=7.5 Hz), 2.25 (s, 3H), 2.08 (s, 3H), 1.99–1.93 (m, 1H), 1.69–1.64 (m, 1H). Mass spectrum (LCMS, ESI) calcd. for C$_{21}$H$_{29}$N$_7$O$_3$: 428 (M+H). Found: 428.

Example 2

2-[3-(2,2-Difluoro-2-phenylethylamino)-6-methyl-2-oxo-2H-pyrazin-1-yl]-N-(3-imino-[1,2,4]oxadiazinan-6-ylmethyl)-acetamide trifluoroacetate

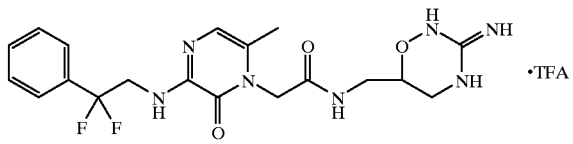

1. Ethyl N-(ethyloxalyl)glycinate

A stirred mixture of glycine ethyl ester hydrochloride (25 g, 0.179 mmol), diethyl oxalate (53 g, 0.358 mmol) and triethylamine (25 mL, 0.179 mmol) in ethanol (75 mL) was warmed up to 50° C. After 20 minutes, all components dissolved and after 5 hours the solvent was removed under vacuum. The residual mass was partitioned between water (250 mL) and dichloromethane (250 mL), and the aqueous layer was extracted with dichloromethane (2×60 mL). The combined organic layers were washed with brine and dried over $Na_2SO_4$. After removal of solvent, the excess diethyl oxalate was removed under high vacuum at 60° C. to give the title compound as a colorless oil (solidified upon standing, 36 g, 100%). $^1$H NMR (400 MHz, $CDCl_3$) δ 7.60 (s(br), 1H), 4.37 (q, 2H, J=7.1 Hz), 4.25 (q, 2H, J=7.1 Hz), 4.12 (d, 2H, J=5.5 Hz), 1.39 (t, 3H, J=7.1 Hz), 1.30 (t, 3H, J=7.1 Hz).

2. N-(Ethoxycarbonylmethyl)-N'-(2-hydroxy-1-propyl)oxamide

To a stirred solution of ethyl N-(ethyloxalyl)gylcinate (18.5 g, 91 mmol), as prepared in the preceding step, in ethanol (80 mL) was added 1-amino-2-propanol (7.0 mL, 91 mmol) under nitrogen. The reaction mixture solidified over a period of 2 hours with stirring. After removal of solvent, the residue was dissolved in dichloromethane (100 mL) and rotovaped. The process was repeated twice. The residue was dried under high vacuum to give the title compound as a white solid (20 g, 95%). $^1$H NMR (400 MHz, $CDCl_3$) δ 7.94 (s (br), 1H), 7.82 (s(br), 1H), 4.24 (q, 2H, J=7.1 Hz), 4.08 (d, 2H, J=5.8 Hz), 3.97 (s(br), 1H), 3.49 (m, 1H), 3.22 (m, 1H), 2.38 (s, 1H),1.30 (t, 3H, J=7.1 Hz), 1.23 (t, 3H, J=7.2 Hz).

3. N-(Ethoxycarbonylmethyl)-N'-(2-oxo-1-propyl)oxamide

To a stirred solution of N-(ethoxycarbonyl-methyl)-N'-(2-hydroxy-1-propyl)oxamide (8.0 g, 34.5 mmol), as prepared in the preceding step, in water (50 mL) under nitrogen at 50° C. was added ruthenium (III) chloride hydrate (75 mg, 0.35 mmol). The reaction flask was removed from the heating bath, and a solution of sodium bromate (5.2 g, 34.5 mmol) in water (40 mL) was added dropwise. The reaction mixture was allowed to cool to room temperature, and then diluted with ethyl acetate and brine. The aqueous layer was extracted with ethyl acetate (2×), then saturated with sodium chloride and extracted again (×2). The combined ethyl acetate layers were washed with brine, dried over $Na_2SO_4$, and treated with activated carbon. Evaporation of the solvent and drying under high vacuum provided the title compound as a white solid (7.3 g, 92%). $^1$H NMR (400 MHz, $CDCl_3$) δ 7.99 (s(br), 1H), 7.84 (s(br), 1H), 4.24 (q, 2H, J=7.1 Hz), 4.19 (d, 2H, J=5.2 Hz), 4.10 (d, 2H, J=5.7 Hz), 2.24 (s, 3H), 1.30 (t, 3H, J=7.1 Hz).

4. 1-(Ethoxycarbonylmethyl)-3-hydroxy-6-methylpyrazinone

To a stirred solution of N-(ethoxycarbonylmethyl)-N'-(2-oxo-1-propyl) oxamide (6.9 g, 30 mmol), as prepared in the preceding step, trifluoroacetic acid (2.32 mL, 30 mmol) and trifluoroacetic anhydride (4.3 mL, 30 mmol) in acetic acid (100 mL) was heated to 80° C. under nitrogen for 10 hours. Additional trifluoroacetic acid (1.5 mL, 20 mmol) and trifluoroacetic anhydride (3.0 mL, 20 mmol) were added, the mixture was stirred at 80° C. for additional 24 hours under nitrogen. After cooling to room temperature, the solvent was removed under reduced pressure. The residue was stirred with acetic acid (13 mL) for 15 minutes at 60° C., then ethyl acetate and hexane (4:1, 60 mL) were added dropwise to the warm mixture. The precipitates were allowed to cool to room temperature, filtered, and dried under high vacuum to give the title compound as an off-white solid (4.9 g, 77%). $^1$H NMR (400 MHz, $CDCl_3$) δ 11.20 (s(br), 1H), 6.17 (s, 1H), 4.66 (s, 2H), 4.24 (q, 2H, J=7.1 Hz), 2.27 (s, 3H), 1.30 (t, 3H, J=7.1 Hz).

5. 3-Bromo-1-(ethoxycarbonylmethyl)-6-methylpyrazinone

A slurry of 1-(ethoxycarbonylmethyl)-3-hydroxy-6-methylpyrazinone (4.24 g, 20 mmol), as prepared in the preceding step, and phosphorous oxybromide (6.3 g, 22 mmol) in chloroform (15 mL) was stirred at 50° C. under nitrogen for 2 hours, then allowed to cool to room temperature overnight. The reaction mixture was diluted with dichloromethane and ice-water, basified with ammonium hydroxide, and extracted with dichloromethane. The combined organic layers were washed with brine, dried over $Na_2SO_4$, treated with activated carbon, filtered and concentrated. The solid was collected, washed with 15% ethyl acetate in hexane, and dried under high vacuum to give the title compound as an orange colored solid (5.1 g, 93%). $^1$H NMR (400 MHz, $CDCl_3$) δ 7.06 (s, 1H), 4.77 (s, 2H), 4.26 (q, 2 H, J=7.1 Hz), 2.24 (s, 3H), 1.31 (t, 3H, J=7.1 Hz).

6. 2,2-Difluoro-2-phenylacetamide

To a stirred 2.46 mL (15.5 mmol) of ethyl benzoylformate was added (diethylamino)sulfur trifluoride (5.0 g, 31 mmol) in one portion. After stirring for 4 hours under nitrogen, the reaction mixture was carefully poured into ice-water, extracted with dichloromethane (×3). The combined organic layers were washed with brine, dried over $Na_2SO_4$, and concentrated to give a pale amber oil. The oil was dissolved in anhydrous ethanol (25 mL) and saturated with gaseous ammonia for 0.5 hours in a pressure flask. The flask was then stopped and allowed to stand overnight. The solvent was removed to give a yellow solid that was crystallized by dissolving in 10 mL of warm ethyl acetate, and adding 30 mL of hot hexane. After cooling for several hours, the crystals were collected by filtration, washed with 1:4 ethyl acetate:hexane, and dried under high vacuum to give the title compound as a tan solid (2.5 g, 94%). $^1$H NMR (400 MHz, $CDCl_3$) δ 7.61 (m, 2H), 7.47 (m, 3H), 6.40 (s(br), 1H), 6.34 (s(br), 1H).

7. 2,2-Difluoro-2-phenylethylamine 2,2-Difluoro-2-phenylacetamide (2.4 g, 14 mmol), as prepared in the preceding step, was dissolved in tetrahydrofuran (30 mL) and cooled to 0° C. To this stirred solution was added 1.0 M borane in tetrahydrofuran (35 mL, 35 mmol) dropwise in 30 minutes, and the reaction mixture was refluxed for 16 hours. After cooling to room temperature, a solution of potassium carbonate (5 g) in water (20 mL) was added to the reaction mixture. The mixture was concentrated in vacuo to about 50 mL and extracted with dichloromethane (3×50 mL). The dichloromethane layer was washed with brine, dried over $Na_2SO_4$, and concentrated in vacuo. The residue was then purified by flash column chromatography (1:1 ethyl acetate:hexane) to give the title compound as a pale yellow oil (900 mg, 41%). $^1$H NMR (400 MHz, $CDCl_3$) δ 7.45 (m, 5H), 3.18 (t, 2H, J=14.5 Hz), 1.60 (s(br), 2H).

8. 3-(2,2-Difluoro-2-phenylethylamino)-1-(ethoxycarbonylmethyl)-6-methylpyrazinone To a stirred suspension of 3-bromo-1-(ethoxycarbonylmethyl)-6-methylpyrazinone (750 mg, 2.75 mmol), as prepared in step 5 of Example 2, in toluene (30 mL) was added 2,2-difluoro-2-phenylethylamine (900 mg, 5.75 mmol), as prepared in the preceding step. The mixture was refluxed for two days under nitrogen. The solution was allowed to cool to room temperature, and ethyl acetate (50 mL) was added. The diluted reaction mixture was washed with 10% HCl (2×20 mL) and the aqueous layer was extracted with ethyl acetate (3×20 mL). The combined organic layers were washed with 10% citric acid (50 mL), brine, and dried over $Na_2SO_4$. After evaporating the solvent, the solid was collected and washed with 15% ethyl acetate in hexane to give the title compound as an off-white solid (730 mg, 76%). $^1$H NMR (400 MHz, $CDCl_3$) δ 7.54 (m, 2H), 7.43 (m, 3H), 6.67 (s, 1H ), 6.14 (s(br), 1H), 4.70 (s, 2H), 4.24 (q, 2H, J=7.1 Hz), 4.09 (td, 2 H, J=14.3, 6.5 Hz), 2.11 (s, 3H), 1.29 (t, 3H, J=7.1 Hz).

9. 1-[Bisbenzylamino]-3-(4-methoxyphenoxy)propan-2-ol

A solution of glycidyl 4-methoxyphenyl ether (1.10 g, 6.10 mmol), dibenzylamine (1.25 g, 6.33 mmol), and anhydrous ethyl alcohol (20 mL) was heated at 80° C. for 2 days. The solvent was evaporated under reduced pressure to give the title compound as a clear oil (2.36 g, 100%). $^1$H NMR ($CDCl_3$) δ 7.35–7.30 (m, 7H), 7.28–7.25 (m, 3H), 6.82–6.76 (m, 4H), 4.10–4.07 (m, 1H), 3.83–3.81 (m, 3H), 3.78–3.76 (m, 1H), 3.76 (s, 3H), 3.53 (d, 2H, J=13.4 Hz), 2.66 (d, 2H, J=6.5 Hz). Mass spectrum (LCMS, ESI) calcd. for $C_{24}H_{27}NO_3$: 378 (M+H). Found: 378.

10. N-[2-Hydroxy-3-(4-methoxyphenoxy)propyl](phenylmethoxy)carboxamide

A mixture of 1-[bisbenzylamino]-3-(4-methoxyphenoxy)propan-2-ol (1.26 g, 3.74 mmol), as prepared in the preceding step, 10% palladium on carbon (125 mg) and methanol (120 mL) was degassed under reduced pressure and refilled with $H_2$ gas several times. After stirring under 1 atm $H_2$ balloon at room temperature overnight, the mixture was filtered through Celite and washed with methanol. The filtrate was concentrated to a white solid (0.78 g, 100%). This solid (0.78 g, 3.96 mmol) was dissolved in methanol (20 mL), dichloromethane (20 mL), and water (10 mL). To this solution were added sodium bicarbonate (0.83 g, 9.88 mmol) and benzyl chloroformate (0.7 mL, 4.66 mmol) at room temperature. After stirring for 4 hours, the solution was concentrated and the residue was partitioned between dichloromethane and water. The organic layer was dried ($Na_2SO_4$), concentrated, and flash chromatographed on silica gel to give the title compound as a white solid (1.00 g, 80.8%). $^1$H NMR ($CDCl_3$) δ 7.37–7.33 (m, 5H), 6.83 (s, 4H), 5.20 (m, 1H), 5.12 (s, 2H), 4.10 (m, 1H), 3.94–3.88 (m, 2H), 3.77 (s, 3H), 3.53–3.47 (m, 1H), 3.38–3.27 (m, 1H), 2.95 (m, 1H).

11. N-[2-(1,3-Dioxoisoindolin-2-yloxy)-3-(4-methoxyphenoxy)propyl]-(phenylmethoxy)carboxamide To a solution of the product (1.00 g, 3.02 mmol) of the preceding step, triphenylphosphine (1.03 g, 3.93 mmol), N-hydroxyphthalimide (0.54 g, 3.31 mmol), and tetrahydrofuran (100 mL) was added diethyl azodicarboxylate (0.62 mL, 3.94 mmol) at 4° C. After stirred at 4° C. to room temperature overnight, the solution was concentrated in vacuo and flash chromatographed ($SiO_2$) to provide the title compound, which was contaminated with 1,2-dicarbethoxyhydrazine, as a yellow semi-solid (1.79 g). $^1$H NMR ($CDCl_3$) δ 7.85 (m, 2H), 7.78 (m, 2H), 7.41–7.31 (m, 5H), 6.82–6.78 (m, 4H), 6.07 (m, 1H), 5.16 (d, 2H, J=3.2 Hz), 4.53 (m, 1H), 4.28–4.25 (m, 1H), 3.76 (s, 3H), 3.74–3.66 (m, 2H).

12. N-[2-(1,3-Dioxoisoindolin-2-yloxy)-3-hydroxypropyl](phenylmethoxy)-carboxamide To a solution of the product (53 mg, 0.10 mmol) of the preceding step in acetonitrile (4 mL) and water (1 mL) at 4° C. was added ammonium cerium nitrate (150 mg, 0.274 mmol). After 15 minutes at 4° C., ethyl acetate and brine were added. The organic layer was separated and the aqueous layer was extracted with ethyl acetate. The combined organic layers were washed with saturated sodium hydrogensulfite and sodium bicarbonate. Drying ($Na_2SO_4$), concentration, and flash chromatography produced the title compound as a yellow oil (40 mg, 96.7%). $^1$H NMR ($CDCl_3$) δ 7.88–7.85 (m, 2H), 7.82–7.78 (m, 2H), 7.41–7.30 (m, 5H), 6.08 (m, 1H), 5.16 (s, 2H), 4.28–4.24 (m, 1H), 3.78–3.72 (m, 3H), 3.59–3.46 (m, 2H).

13. tert-Butyl-2-aza-3-[(tert-butoxy)carbonylamino]-3-[(2-hydroxy-1-{[(phenylmethoxy)carbonylamino]methyl}ethoxy)amino]prop-2-enoate The product (650 mg, 1.76 mmol) of the preceding step in methanol (15 mL) was treated with 40 wt. % methylamine in water (680 mg, 8.77 mmol) for 2 hours at room temperature. After removal of the solvents under reduced pressure, the remaining brown solid was dissolved in anhydrous N,N-dimethylformamide (20 mL) and reacted with N,N'-bis(tert-butoxycarbonyl)-1H-pyrazole-1-carboxamidine (1.09 g, 3.52 mmol) at 50° C. overnight. The solution was concentrated and flash chromatographed ($SiO_2$) to provide the title compound as an orange oil (776 mg, 91.6%, 2 steps). $^1$H NMR ($CDCl_3$) δ 9.12 (s, 1H), 7.67 (s,1H), 7.36–7.33(m, 5H), 5.60 (m, 1H), 5.12 (s, 2H), 4.19 (m, 1H), 3.87–3.76 (m, 2H), 3.56 (t, 2H, J=5.9 Hz), 1.50 (s, 9H), 1.46 (s, 9H).

14. tert-Butyl 2-aza-2-(4-[(tert-butyl)oxycarbonyl]-6-{[(phenylmethoxy)-carbonylamino]methyl}(1,2,4-oxadiazaperhydroin-3-ylidene))acetate To a solution of the product (770 mg, 1.60 mmol), as prepared in the preceding step, triphenylphosphine (840 mg, 3.21 mmol), and tetrahydrofuran (50 mL) was added diethyl azodicarboxylate (0.500 mL, 3.18 mmol) at 4° C. After 20 minutes at 4° C., the cooling bath was removed and the solution was stirred at room temperature for 3 hours. Concentration and flash chromatography yielded the title compound as a yellow oil (702 mg, 94.7%). $^1$H NMR ($CDCl_3$) δ 8.10 (s, 1H), 7.35 (s, 5H), 5.33 (t, 1H, J=5.8 Hz), 5.10 (s, 2H), 3.99–3.91 (m, 2H), 3.62–3.57 (m, 1H), 3.44 (dd, 1H, J=9.4, 12.0 Hz), 3.32–3.27 (m, 1H), 1.51 (s, 9H), 1.47 (s, 9H). Mass spectrum (LCMS, ESI) calcd. for $C_{22}H_{32}N_4O_7$: 487 (M+Na). Found: 487.

15. tert-Butyl 2-{6-(aminomethyl)-4-[(tert-butyl)oxycarbonyl](1,2,4-oxadiazaperhydroin-3-ylidene)}-2-azaacetate The mixture of the product (702 mg, 1.51 mmol) of the preceding step, 10% palladium on carbon (80 mg), and methanol (30 mL) was degassed under reduced pressure and refilled with $H_2$ gas several times. The mixture was stirred under 1 atm $H_2$ balloon at room temperature for 5 hours. After concentration and flash chromatography on silica gel, the title compound was obtained as white foam (205 mg, 41.1%). $^1$H NMR ($CDCl_3$) δ 5.55 (s, 1H), 3.92–3.88 (m, 1H), 3.59–3.44 (m, 3H), 3.05–2.91 (m, 1H), 1.51 (s, 9H), 1.47 (s, 9H).

16. tert-Butyl 2-aza-2-{6-[(2-{3-[(2,2-difluoro-2-phenylethyl)-amino]-6-methyl-2-oxohydropyrazinyl}acetylamino)methyl]-4-[(tert-butyl)oxycarbonyl](1,2,4-oxadiazaperhydroin-3-ylidene)}acetate 3-(2,2-Difluoro-2-phenylethylamino)-1-(ethoxycarbonylmethyl)-6-methylpyrazinone (474 mg, 1.35 mmol), as prepared in step 8 of Example 2, in methanol (20 mL) and water (10 mL) was treated with potassium hydroxide (226 mg, 4.04 mmol) overnight. The mixture was acidified with 10% HCl until acidic to pH paper and then concentrated. The residue was partitioned between dichloromethane and brine. The organic phase was dried ($Na_2SO_4$) and concentrated to give a white solid. To the white solid in N,N-dimethylformamide (10 mL) was added tert-butyl 2-{6-(aminomethyl)-4-[(tert-butyl)oxycarbonyl](1,2,4-oxadiazaperhydroin-3-ylidene)}-2-azaacetate (562 mg, 1.70 mmol), as prepared in the preceding step, N,N-diisopropylethylamine (800 mg, 6.20 mmol) and Castro's reagent (822 mg, 1.86 mmol). After stirring at room temperature overnight, the reaction solution was concentrated and the residue was partitioned between dichloromethane and 10% citric acid (×2). The combined organic phases were dried ($Na_2SO_4$), concentrated, and flash chromatographed ($SiO_2$) to provide the title compound as a yellow oil (920 mg, 100%). $^1$H NMR (CDCl$_3$) δ 9.41 (s(br), 1H), 8.01 (s, 1H), 7.53–7.50 (m, 2H), 7.43–7.37 (m, 3H), 7.15 (m, 1H), 6.68 (s, 1H), 6.26 (t, 1H, J=6.4 Hz), 4.67 (dd, 2H, J=15.8, 28.4 Hz), 4.07–3.98 (m, 3H), 3.89 (dd, 1H, J=3.3, 12.2 Hz), 3.61–3.59 (m, 1H), 3.58–3.36 (m, 2H), 2.15 (s, 3H), 1.51 (s, 9H), 1.45 (s, 9H).

17. 2-[3-(2,2-Difluoro-2-phenylethylamino)-6-methyl-2-oxo-2H-pyrazin-1-yl]-N-(3-imino-[1,2,4]oxadiazinan-6-ylmethyl)-acetamide trifluoroacetate A solution of the product of the preceding step (920 mg, 1.45 mmol) in trifluoroacetic acid (3 mL) and dichloromethane (9 mL) was stirred at room temperature overnight and concentrated. The residue was purified by flash chromatography ($SiO_2$) and lyophilized to provide the title compound as a off-white powder (570 mg, 90.4%). $^1$H NMR (DMSO-d$_6$) δ 10.77 (s, 1H), 7.92 (s, 1H), 7.73 (s, 1H), 6.67 (s, 3H), 6.63 (s, 3H), 6.23 (s, 1H), 5.77 (s, 1H), 3.75 (s, 2H), 3.24–3.12 (m, 3H), 2.68 (d, 1H, J=11.2 Hz), 2.26 (t, 1H, J=10.7 Hz), 1.62 (s, 2H), 1.19 (s, 3H). Mass spectrum (LCMS, ESI) calcd. for $C_{19}H_{23}F_2N_7O_3$: 436 (M+H). Found: 436.

Example 3

Tablet Preparation

Tablets containing 25.0, 50.0, and 100.0 mg, respectively, of the following active compounds are prepared as illustrated below:

a. N-(2-carbamimidoyl-[1,2]oxazinan-5-yl)-2-[6-methyl-2-oxo-3-(2-p-tolylethylamino)-2H-pyrazin-1-yl]-acetamide trifluoroacetate; and b. 2-[3-(2,2-difluoro-2-phenylethylamino)-6-methyl-2-oxo-2H-pyrazin-1-yl]-N-(3-imino-[1,2,4]oxadiazinan-6-ylmethyl)-acetamide trifluoroacetate.

Tablet for Doses Containing from 25–100 MG of the Active Compound

|  | Amount-mg | | |
| --- | --- | --- | --- |
| Active Compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

Example 4

Intravenous Solution Preparation

An intravenous dosage form of the above-indicated active compounds is prepared as follows:

| Active Compound | 0.5–10.0 mg |
| --- | --- |
| Sodium Citrate | 5–50 mg |
| Citric Acid | 1–15 mg |
| Sodium Chloride | 1–8 mg |
| Water for Injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

Example 5

In vitro Inhibition of Purified Enzymes

Reagents: All buffer salts were obtained from Sigma Chemical Company (St. Louis, Mo.), and were of the highest purity available. The enzyme substrates, N-benzoyl-Phe-Val-Arg-p-nitroanilide (Sigma B7632), N-benzoyl-Ile-Glu-Gly-Arg-p-nitroanilide hydrochloride (Sigma B2291), N-p-Tosyl-Gly-Pro-Lys-p-nitroanilide (Sigma T6140), N-succinyl-Ala-Ala-Pro-Phe-p-nitroanilide (Sigma S7388) and N—CBZ-Val-Gly-Arg-p-nitroanilide (Sigrna C7271) were obtained from Sigma. N-succinyl-Ala-Ala-Pro-Arg-p-nitroanilide (BACHEM L-1720) and N-succinyl-Ala-Ala-Pro-Val-p-nitroanilide (BACHEM L-1770) were obtained from BACHEM (King of Prussia, Pa.).

Human α-thrombin, human factor Xa and human plasmin were obtained from Enzyme Research Laboratories (South Bend, Indiana). Bovine α-chymotrypsin (Sigma C4129), bovine trypsin (Sigma T8642) and human kidney cell urokinase (Sigma U5004) were obtained from Sigma. Human leukocyte elastase was obtained from Elastin Products (Pacific, Mo.).

$K_i$ Determinations: All assays are based on the ability of the test compound to inhibit the enzyme catalyzed hydrolysis of a peptide p-nitroanilide substrate. In a typical $K_i$ determination, substrate is prepared in DMSO, and diluted into an assay buffer consisting of 50 mM HEPES, 200 mM NaCl, pH 7.5. The final concentrations for each of the substrates is listed below. In general, substrate concentrations are lower than the experimentally determined value for $K_m$. Test compounds are prepared as a 1.0 mg/ml solution in DMSO. Dilutions are prepared in DMSO yielding 8 final concentrations encompassing a 200 fold concentration range. Enzyme solutions are prepared at the concentrations listed below in assay buffer.

In a typical $K_i$ determination, into each well of a 96 well plate is pipetted 280 mL of substrate solution, 10 mL of test compound solution, and the plate allowed to thermally equilibrate at 37° C. in a Molecular Devices plate reader for >15 minutes. Reactions were initiated by the addition of a 10 mL aliquot of enzyme and the absorbance increase at 405 nm is recorded for 15 minutes. Data corresponding to less than 10% of the total substrate hydrolysis were used in the calculations. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined K, value.

Thrombin: Thrombin activity was assessed as the ability to hydrolyze the substrate N-succinyl-Ala-Ala-Pro-Arg-p-nitroanilide. Substrate solutions were prepared at a concentration of 32 mM (32 mM<<Km=180 mM) in assay buffer. Final DMSO concentration was 4.3%. Purified human α-thrombin was diluted into assay buffer to a concentration of 15 nM. Final reagent concentrations were: [thrombin]= 0.5 mM, [substrate N-succinyl-Ala-Ala-Pro-Arg-p-nitroanilide]=32 mM.

Factor X [FXa]: FXa activity was assessed as the ability to hydrolyze the substrate N-benzoyl-Ile-Glu-Gly-Arg-p-nitroanilide hydrochloride. Substrate solutions were prepared at a concentration of 51 mM (51<<$K_m$=1.3 mM) in assay buffer. Final DMSO concentration was 4.3%. Purified activated human Factor X was diluted into assay buffer to a concentration of 300 nM. Final reagent concentrations were: [FXa]=10 nM, [N-benzoyl-Ile-Glu-Gly-Arg-p-nitroanilide hydrochloride]=51 mM.

Plasmin: Plasmin activity was assessed as the ability to hydrolyze the N-p-Tosyl-Gly-Pro-Lys-p-nitroanilide. Substrate solutions were prepared at a concentration of 37 mM (37 mM<<$K_m$=243 mM) in assay buffer. Final DMSO concentration was 4.3%. Purified human plasmin was diluted into assay buffer to a concentration of 240 nM. Final reagent concentrations were: [Plasmin]=8 nM, [N-p-Tosyl-Gly-Pro-Lys-p-nitroanilide]=37 mM.

Chymotrypsin: Chymotrypsin activity was assessed as the ability to hydrolyze N-succinyl-Ala-Ala-Pro-Phe-p-nitroanilide. Substrate solutions were prepared at a concentration of 14 mM (14 mM<<$K_m$=62 mM) in assay buffer. Final DMSO concentration was 4.3%. Purified bovine chymotrypsin was diluted into assay buffer to a concentration of 81 nM. Final reagent concentrations were: [Chymotrypsin]= 2.7 nM, [N-succinyl-Ala-Ala-Pro-Phe-p-nitroanilide]=14 mM.

Trypsin: Trypsin activity was assessed as the ability to hydrolyze N-benzoyl-Phe-Val-Arg-p-nitroanilide. Substrate solutions were prepared at a concentration of 13 mM (13 mM<<$K_m$=291 mM) in assay buffer. Final DMSO concentration was 4.3%. Purified bovine trypsin was diluted into assay buffer to a concentration of 120 nM. Final reagent concentrations were: [Trypsin]=4 nM, [N-benzoyl-Phe-Val-Arg-p-nitroanilide]=13 mM.

Elastase: Elastase activity was assessed as the ability to hydrolyze N-succinyl-Ala-Ala-Pro-Val-p-nitroanilide. Substrate solutions were prepared at a concentration of 19 mM (19 mM<<$K_m$=89 mM) in assay buffer. Final DMSO concentration was 4.3%. Purified human leukocyte elastase was diluted into assay buffer to a concentration of 750 nM. Final reagent concentrations were: [Elastase]=25 nM, [N-succinyl-Ala-Ala-Pro-Val-p-nitroanilide]=19 mM.

Urokinase: Urokinase activity was assessed as the ability to hydrolyze N—CBZ-Val-Gly-Arg-p-nitroanilide. Substrate solutions were prepared at a concentration of 100 mM (100 mM<$K_m$=1.2 mM) in assay buffer. Final DMSO concentration was 4.3%. Purified human kidney urokinase was diluted into assay buffer to a concentration of 1.2 mM. Final reagent concentrations were: [Urokinase]=40 nM, and [N—CBZ-Val-Gly-Arg-p-nitroanilide]=100 mM.

The results of the compound of Examples 1 and 2 are shown in the following table.

TABLE 1

| | Thrombin Assay, $K_i$ (nM) | |
|---|---|---|
| Compound (Eg. No.) | 1 | 2 |
| $K_i$ | 0.6–1.3 | 5.0 |

The results indicate that the compounds of the present invention are potent and highly selective inhibitors of thrombin.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A compound of Formula I:

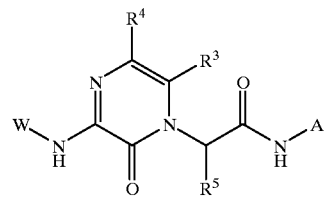

or a hydrate or pharmaceutically acceptable salt thereof; wherein:

W is hydrogen, $R^1$, $R^1OCO$, $R^1CO$, $R^1(CH_2)_sNHCO$, or $(R^1)_2CH(CH_2)_sNHCO$, wherein s is 0–4;

$R^1$ is $R^2$, $R^2(CH_2)_tC(R^{12})_2$, where t is 0–3, and each $R^{12}$ can be the same or different, $(R^2)(OR^{12})CH(CH_2)_p$, where p is 1–4, $(R^2)_2(OR^{12})C(CH_2)_p$, where p is 1–4, $R^2C(R^{12})_2(CH_2)_t$, wherein t is 0–3, each $R^{12}$ can be the same or different, wherein $(R^{12})_2$ can also form a ring with C represented by $C_{3-7}$ cycloalkyl, $R^2CF_2C(R^{12})_2(CH_2)_q$, wherein q is 0–2, and each $R^{12}$ can be the same or different, wherein $(R^{12})_2$, can also form a ring with C represented by $C_{3-7}$ cycloalkyl, $R^2CH_2C(R^{12})_2(CH_2)_q$, wherein q is 0–2, and each $R^{12}$ can be the same or different, wherein $(R^{12})_2$ can also form a ring with C represented by $C_{3-7}$ cycloalkyl, $(R^2)_2CH(CH_2)_r$, where r is 0–4 and each $R^2$ can be the same or different, and wherein $(R^2)_2$ can also form a ring with CH represented by $C_{3-7}$ cycloalkyl, $C_{7-12}$ bicyclic alkyl, $C_{10-16}$ tricyclic alkyl or a 5- to 7-membered mono- or 9- or 10- membered bicyclic heterocyclic ring which is selected from the group consisting of piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl, $R^2O(CH_2)_p$, wherin p is 2–4, $(R^2)_2CF(CH_2)_r$, wherein r is 0–4 and each $R^2$ can be the same or different, wherein $(R^2)_2$ can also form a ring with C represented by $C_{3-7}$ cycloalkyl, $C_{7-2}$ bicyclic alkyl, $C_{10-16}$ tricyclic alkyl, or a 5- to 7-membered mono- or 9- or 10- membered bicyclic heterocyclic ring which is selected from the group consisting of piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl,

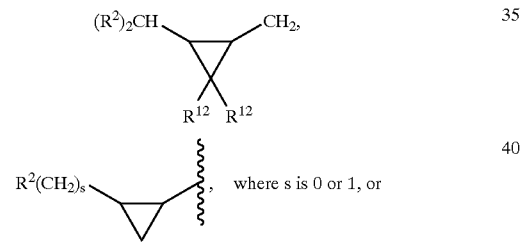

$R^2CF_2C(R^{12})_2$;

$R^2$ is phenyl, naphthyl, or biphenyl, each of which is unsubstituted or substituted with one or more of $C_{1-4}$ alkyl, $C_{1-4}$ alkoxy, halogen, hydroxy, $CF_3$, $OCF_3$, COOH, $CONH_2$, or $SO_2NH_2$, a 5- to 7-membered mono- or a 9- to 10-membered bicyclic heterocyclic ring or non-heterocyclic ring which can be saturated or unsaturated, wherein the heterocyclic ring is selected from the group consisting of piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl, each of which is optionally substituted with halogen or hydroxy, and wherein the heterocyclic or non-heterocyclic ring is unsubstituted or substituted with halogen or hydroxy, $C_{1-7}$ alkyl, unsubstituted or substituted with one or more of hydroxy, COOH, amino, aryl, $C_{3-7}$ cycloalkyl, $CF_3$, $N(CH_3)_2$, or $C_{1-3}$ alkylaryl, $CF_3$, $C_{3-7}$ cycloalkyl, unsubstituted or substituted with aryl, $C_{7-12}$ bicyclic alkyl, or $C_{10-16}$ tricyclic alkyl;

$R^3$ is hydrogen, $C_{1-6}$ alkyl, $C_{3-7}$ cycloalkyl, $C_{2-6}$ alkynyl, optionally substituted $C_{6-10}$ aryl, optionally substituted $C_{6-10}$ ar($C_{1-6}$)alkyl, trifluoromethyl, halogen, $C_{1-6}$ hydroxyalkyl, cyano, nitro, carboxamido, —$CO_2R^x$, —$CH_2OR^x$ or —$OR^x$, where $R^x$, in each instance, is independently one of hydrogen, $C_{1-6}$ alkyl or $C_{3-7}$ cycloalkyl wherein said alkyl or cycloalkyl groups may optionally have one or more unsaturations;

$R^4$ is hydrogen or halogen;

$R^{12}$ is hydrogen phenyl, naphthyl, or biphenyl, each of which is unsubstituted with one or more of $C_{1-4}$ alkyl, $C_{1-4}$ alkoxy, halogen, hydroxy, $CF_3$, $OCF_3$, COOH, or $CONH_2$, a 5- to 7-membered mono- or a 9- to 10-membered bicyclic heterocyclic ring which is selected from the group consisting of piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl, $C_{1-4}$ alkyl, unsubstituted or substituted with one or more of hydroxy, COOH, amino, or aryl, $CF_3$, $C_{3-7}$ cycloalkyl, $C_{7-12}$ bicyclic alkyl, or $C_{10-16}$ tricyclic alkyl;

$R^5$ is hydrogen, $C_{1-4}$ alkyl, or $C_{2-4}$ alkenyl;

A is one of

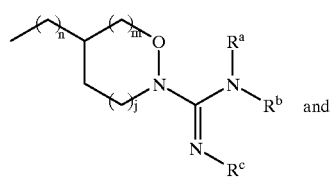 and

R$^a$, R$^b$ and R$^c$ are independently hydrogen, alkyl, hydroxy, alkoxy, aryloxy, aralkoxy, alkoxycarbonyloxy, cyano or —CO$_2$R$^w$, where R$^w$ is alkyl, cycloalkyl, phenyl, benzyl, where R$^d$ and R$^e$ are independently hydrogen, C$_{1-6}$ alkyl, C$_{2-6}$ alkenyl or phenyl, R$^f$ is hydrogen, C$_{1-6}$ alkyl, C$_{2-6}$ alkenyl or phenyl, R$^g$ is hydrogen, C$_{1-6}$ alkyl, C$_{2-6}$ alkenyl or phenyl, and R$^h$ is aralkyl or C$_{1-6}$ alkyl;

each n is from zero to 4;
each m is from zero to 4; and
each j is from zero to 4;
provided that n, m and j are not all zero.

2. A compound of claim 1, wherein
R$^3$ is hydrogen, C$_{1-4}$ alkyl, C$_{3-7}$ cycloalkyl or CF$_3$;
m is from zero to 2;
n is from zero to 2; and
j is from zero to 2, provided that n, m and j are not all zero.

3. A compound of claim 2, wherein R$^3$ is C$_{1-4}$ alkyl.

4. A compound of claim 2, wherein R$^4$ is hydrogen or halogen.

5. A compound of claim 4, wherein W is H or R$^1$.

6. A compound of claim 5, wherein
R$^1$ is
R$^2$,
R$^2$(CH$_2$)$_t$C(R$^{12}$)$_2$, wherein t is 0–3 and each R$^{12}$ can be the same or different,
R$^2$C(R$^{12}$)$_2$(CH$_2$)$_t$, wherein t is 0–3, each R$^{12}$ can be the same or different and wherein (R$^{12}$)$_2$ can also form a 3- to 7-membered cycloalkyl ring the C to which they are attached,
R$^2$CH$_2$C(R$^{12}$)$_2$(CH$_2$)$_q$, wherein q is 0–2, and each R$^{12}$ is the same or different, and wherein (R$^{12}$)$_2$, together with the C to which they are attached, cam also form a 3- to 7-membered cycloalkyl ring,
(R$^2$)CH(CH$_2$)$_r$, wherein r is 0–4, R$^2$ can be the same or different and wherein (R$^2$)$_2$ can also form, together with the C to which they are attached, a C$_{3-7}$ cycloalkyl, C$_{7-12}$ bicycloalkyl, C$_{10-16}$ tricycloalkyl or 5- to 7-membered saturated or unsaturated mono or 9- to 10-membered bicyclic heterocycle selected from the group consisting of piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl and benzodioxolyl,
R$^2$CF$_2$C(R$^{12}$)$_2$(CH$_2$)$_q$, wherein q is 0–2, and each R$^{12}$ is the same or different, and wherein (R$^{12}$)$_2$, together with the C to which they are attached, can also form a 3- to 7-membered cycloalkyl ring, or
R$^2$O(CH$_2$)$_p$, wherein p is 2–4;

R$^2$ is
phenyl or naphthyl, each of which is optionally substituted with one or more of C$_{1-4}$ alkyl, C$_{1-4}$ alkoxy, halogen, hydroxy CF$_3$, OCF$_3$ or SO$_2$NH$_2$,
a 5- to 7-membered monocyclic or 9- to 10-membered bicyclic, saturated or unsaturated, ring having from zero to 4 heteroatoms selected from N, O and S, wherein heterocyclic ring is selected from the group consisting of piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl and benzodioxolyl, and wherein said ring is optionally substituted with halogen or hydroxy,
C$_{1-7}$ alkyl optionally substituted with one or more of hydroxy, COOH, C$_{3-7}$ cycloalkyl, CF$_3$, N(CH$_3$)$_2$, or C$_{1-3}$ alkylaryl,
CF$_3$, or
C$_{3-7}$ cycloalkyl, optionally substituted with aryl; and R$^{12}$ is
hydrogen, or
C$_{1-4}$ alkyl, optionally substituted with one or more of hydroxy, COOH, amino, or aryl.

7. A compound of claim 6, wherein
R$^3$ is hydrogen, CH$_3$ or CH$_2$CH$_3$;
R$^4$ is hydrogen or chloro; and
W is PhCH$_2$CH$_2$, (CH$_3$)$_3$C, HOOCCH$_2$, CF$_3$CH$_2$, (CH$_3$)$_2$N(CH$_2$)$_2$, PhCH$_2$O(CH$_2$)$_2$, PhCH(CH$_3$), PhCH$_2$CH(COOH), CH$_3$(CH$_2$)$_5$, PhCH$_2$, H, CH$_3$(CH$_2$)$_4$, CH$_3$CH$_2$CH(CH$_3$)CH$_2$, (Ph)$_2$CHCH$_2$, PhCH$_2$CH(CH$_3$), PhCH(CH$_3$)CH$_2$, (CH$_3$)$_2$CH, PhCH(OH)CH$_2$, PhC(CH$_3$)$_2$CH$_2$, (Ph)$_2$CHCH$_2$, or W is -continued

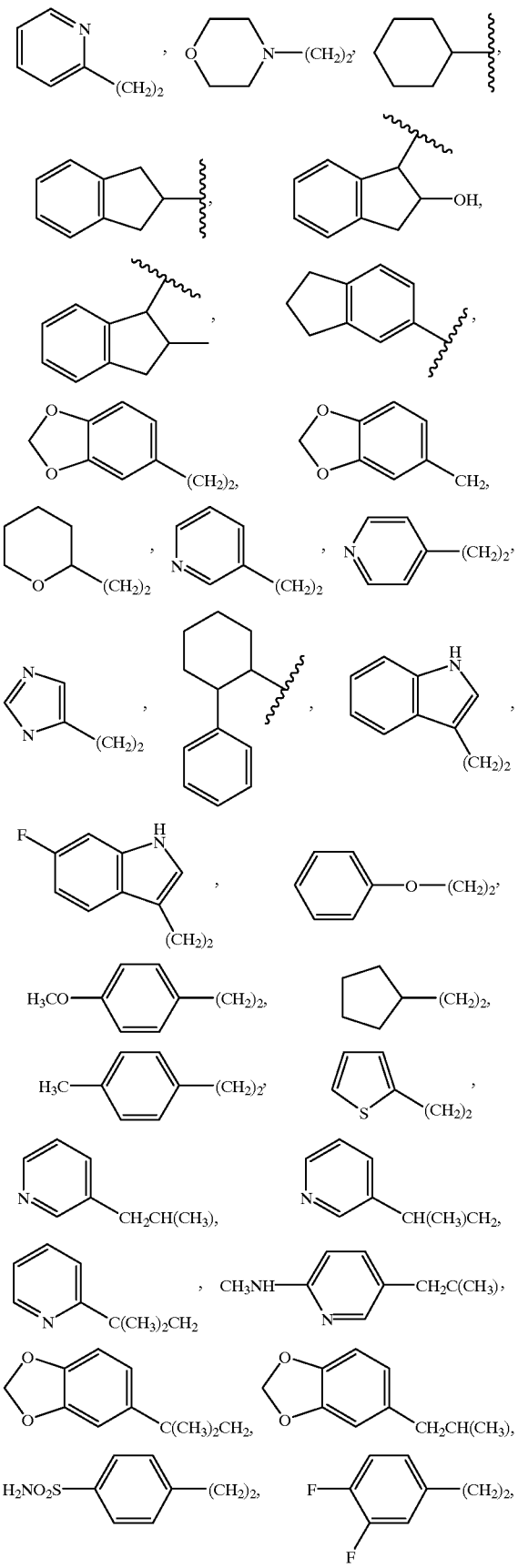

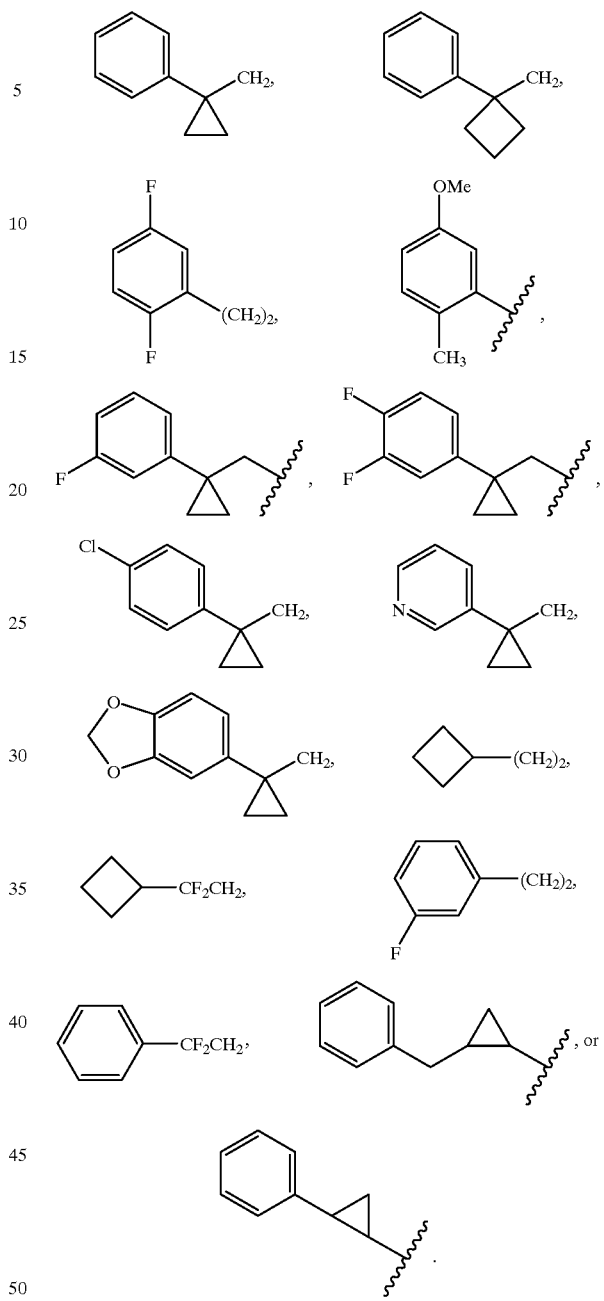

8. A compound of claim 1, wherein $R^5$ is hydrogen.

9. A compound of claim 1, wherein $R^a$, $R^b$ and $R^c$ are independently one of hydrogen, $C_{1-6}$ alkyl, $C_{1-6}$ alkoxy, cyano, or —$CO_2R^w$ where $R^w$, in each instance, is $C_{1-4}$ alkyl, $C_{4-7}$ cycloalkyl or benzyloxycarbonyl.

10. A compound of claim 9, wherein $R^a$, $R^b$ and $R^c$ are independently one of hydrogen, methyl, ethyl, propyl, n-butyl, hydroxy, methoxy, ethoxy, cyano, —$CO_2CH_3$, —$CO_2CH_2CH_3$ or —$CO_2CH_2CH_2CH_3$.

11. A compound of claim 10, wherein $R^a$, $R^b$ and $R^c$ are each hydrogen.

12. A compound of claim 9, wherein $R^a$, $R^b$ and $R^c$ are independently one of

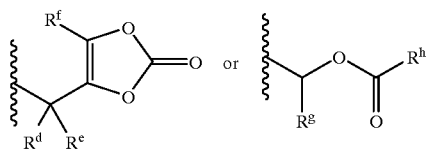 or where $R^d$–$R^h$ are defined as in claim 1.

13. A compound of claim 12, wherein $R^d$, $R^e$ and $R^g$ are each hydrogen;

$R^f$ is methyl; and $R^h$ is benzyl or tert-butyl.

14. A compound of claim 1, having one of Formulae Ia or Ib:

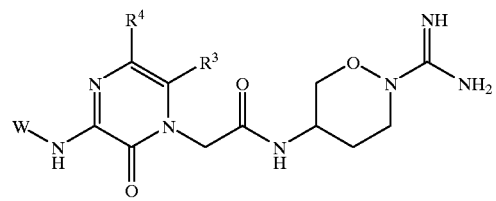

Ia

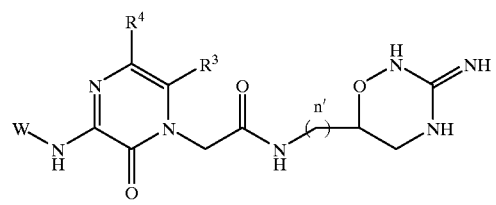

Ib or a hydrate or pharmaceutically acceptable salt thereof, wherein:

W is as defined as in claim 1;

$R^3$ is hydrogen, $C_{1-3}$ alkyl, halogen or $C_{1-2}$ alkoxy;

$R^4$ is hydrogen or halogen; and n' is 0 or 1.

15. A compound of claim 14, wherein
W is $PhCH_2CH_2$, $(CH_3)_3C$, $HOOCCH_2$, $CF_3CH_2$, $(CH_3)_2N(CH_2)_2$, $PhCH_2O(CH_2)_2$, $PhCH(CH_3)$, $PhCH_2CH_2(COOH)$, $CH_3(CH_2)_5$, $PhCH_2$, H, $CH_3(CH_2)_4$, $CH_3CH_2CH(CH_3)CH_2$, $(Ph)_2CHCH_2$, $PhCH_2CH(CH_3)$, $PhCH(CH_3)CH_2$, $(CH_3)_2CH$, $PhCH(OH)CH_2$, $PhC(CH_3)_2CH_2$, $(Ph)_2CHCH_2$, or W is

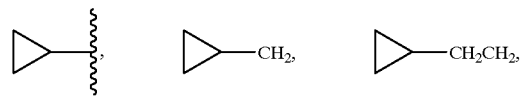

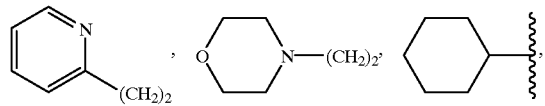

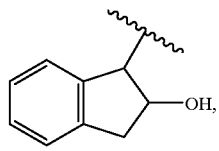

-continued

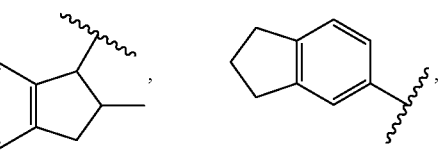

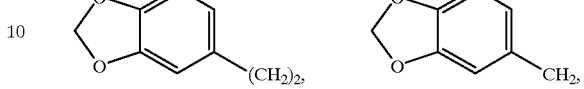

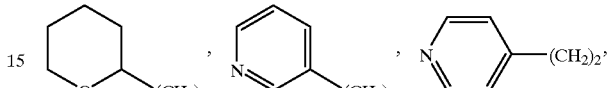

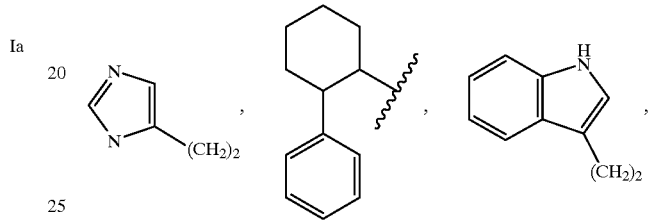

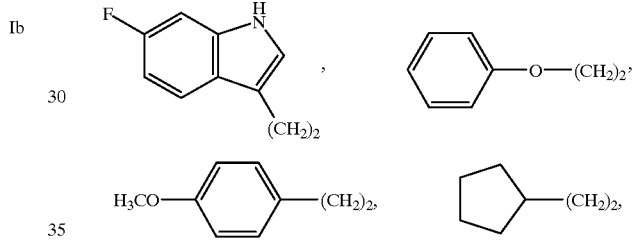

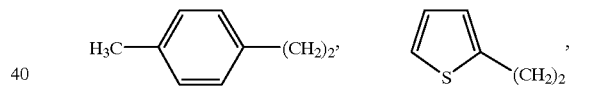

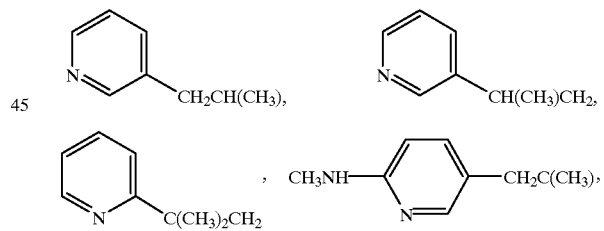

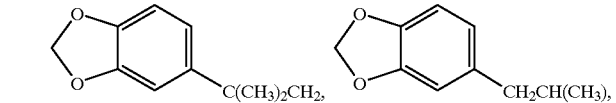

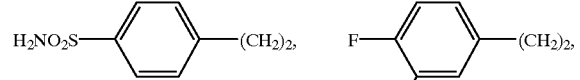

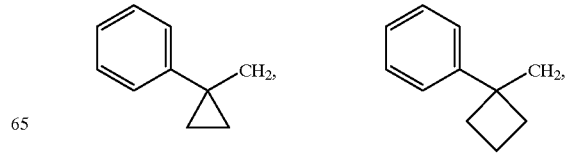

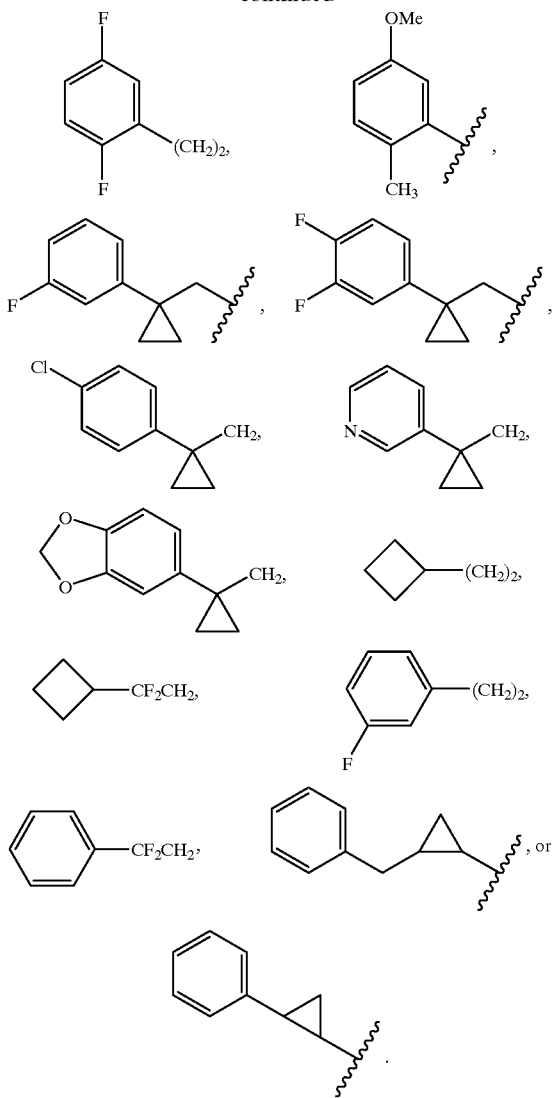

16. A compound of claim 1, which is one of:
N-(2-carbamimidoyl-[1,2]oxazinan-5-yl)-2-(6-methyl-2-oxo-3-phenethylamino)-2H-pyrazin-1-yl)-acetamide;
N-(2-carbamimidoyl-[1,2]oxazinan-5-yl)-2-(5-chloro-6-methyl-2-oxo-3-phenethylamino-2H-pyrazin-1-yl)-acetamide;
N-(2-carbamimidoyl-[1,2]oxazinan-5-yl)-2-[3-(2,2-diphenyl-ethylamino)-6-methyl-2-oxo-2H-pyrazin-1-yl]-acetamide;
N-(2-carbamimidoyl-[1,2]oxazinan-5-yl)-2-[5-chloro-3-(2,2-diphenyl-ethylamino)-6-methyl-2-oxo-2H-pyrazin-1-yl]-acetamide;
N-(2-carbamimidoyl-[1,2]oxazinan-5-yl)-2-{3-[2-(4-methoxy-phenyl)-ethylamino]-methyl-2-oxo-2H-pyrazin-1-yl}-acetamide;
N-(2-carbamimidoyl-[1,2]oxazinan-5-yl)-2-{6-methyl-2-oxo-3-[(1-phenyl-cyclobutylmethyl)-amino]-2H-pyrazin-1-yl}-acetamide;
N-(2-carbamimidoyl-[1,2]oxazinan-5-yl)-2-[6-methyl-3-(2-naphthalen-1-yl-ethylamino)-2-oxo-2H-pyrazin-1-yl]-acetamide;
N-(2-carbamimidoyl-[1,2]oxazinan-5-yl)-2-[6-methyl-2-oxo-3-(2-phenyl-butylamino)-2H-pyrazin-1-yl]-acetamide;
and pharmaceutically acceptable salts thereof.

17. A pharmaceutical composition, comprising a compound of claim 1 and a pharmaceutically acceptable carrier.

18. A pharmaceutical composition, comprising a compound of claim 14 and a pharmaceutically acceptable carrier.

19. A pharmaceutical composition, comprising a compound of claim 16 and a pharmaceutically acceptable carrier.

20. A method of reducing blood coagulation in a mammal, comprising administering a compound of claim 1 to the mammal.

21. The compound N-(2-caramimidoyl-[1,2]oxazinan-5-yl)-2-[6-methyl-2-oxo-3-(2-p-tolylethyl-amino)-2H-pyrazin-1-yl]-acetamide or a hydrate, or pharmaceutically acceptable salt thereof.

22. The compound 2-[3-(2,2-difluoro-2-phenylethylamino)-6-methyl-2-oxo-2H-pyrazin-1-yl]-N-(3-imino-[1,2,4]oxadiazinan-6-ylmethyl)-acetamide or a hydrate, or pharmaceutically acceptable salt thereof.

23. A compound of claim 1, wherein W is $PhCH_2CH_2$, $(CH_3)_3C$, $HOOCCH_2$, $CF_3CH_2$, $(CH_3)_2N(CH_2)_2$, $PhCH_2O(CH_2)_2$, $PhCH(CH_3)$, $PhCH_2CH(COOH)$, $CH_3(CH_2)_5$, $PhCH_2$, H, $CH_3(CH_2)_4$, $CH_3CH_2CH(CH_3)CH_2$, $(Ph)_2CHCH_2$, $PhCH_2CH(CH_3)$, $PhCH(CH_3)CH_2$, $(CH_3)_2CH$, $PhCH(OH)CH_2$, $PhC(CH_3)_2$, or $(Ph)_2CHCH_2$.

24. A compound of claim 1, wherein W is:

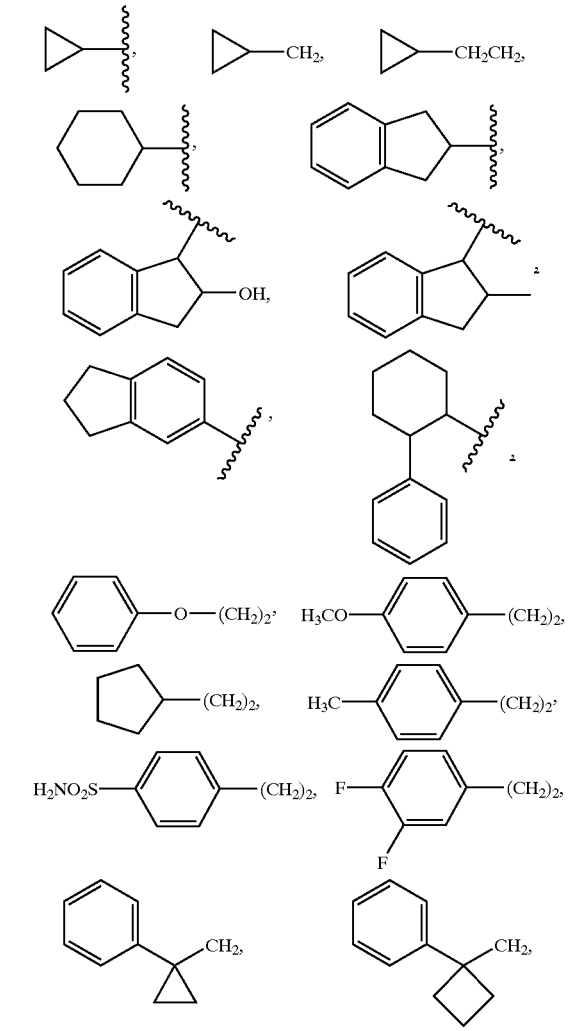

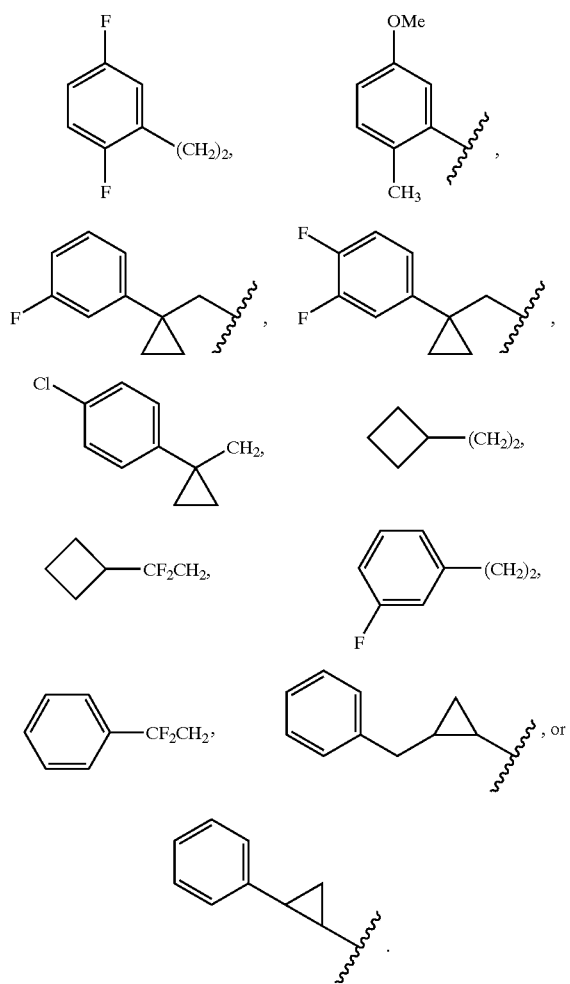
25. a compound of claim 1, wherein W is:
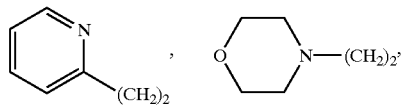
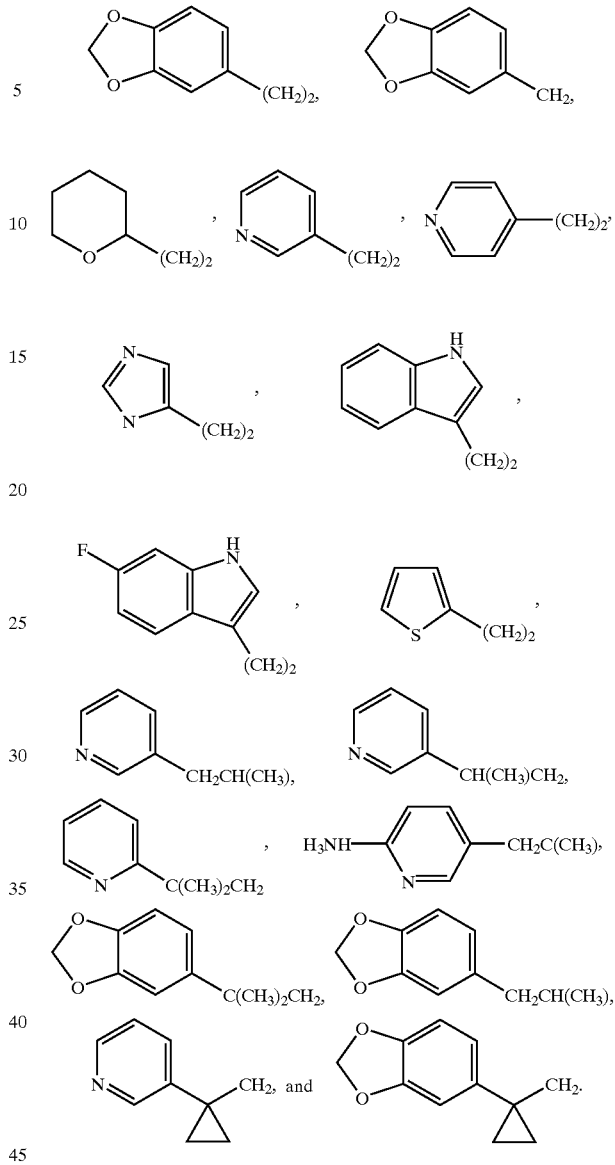
* * * * *

UNITED STATES PATENT AND TRADEMARK OFFICE
CERTIFICATE OF CORRECTION

PATENT NO.     : 6,476,016 B2
DATED          : November 5, 2002
INVENTOR(S)    : Wang et al.

It is certified that error appears in the above-identified patent and that said Letters Patent is hereby corrected as shown below:

Column 45,
Line 16, delete "$C_{7-2}$ bicyclic" and insert therefor -- $C_{7-12}$ bicyclic --.

Column 46,
Line 16, delete "$C_{3-7}$ cycloalkyl, $C_{2-6}$ alkynyl," and insert therefor -- $C_{3-7}$ cycloalkyl, $C_{2-6}$ alkenyl, $C_{2-6}$ alkynyl, --.

Column 47,
Line 48, delete "a 3– to 7-membered cycloalkyl ring the C to which" and insert therefor -- a 3– to 7-membered cycloalkyl ring with the C to which --.

Column 51,
Lines 47-48, delete "$PhCH_2CH_2(COOH)$" and insert therefor -- $PhCH_2CH(COOH)$ --.

Column 53,
Lines 56-58, delete "N-(2-carbamimidoyl-[1,2]oxazinan-5-yl)-2-{3-[2-(4-methoxy-phenyl)-ethylamino]-methyl-2-oxo-2H-pyrazin-1-yl}-acetamide;" and insert therefor -- N-(2-carbamimidoyl-[1,2]oxazinan-5-yl)-2-{3-[2-(4-methoxy-phenyl)-ethylamino]-6-methyl-2-2oxo-2H-pyrazin-1-yl}-acetamide; --.

Column 54,
Lines 11-13, delete "N-(2-caramimidoyl-[1,2]oxazinan-5-yl)-2-[6-methyl-2-oxo-3-(2-p-tolylethyl-amino)-2H-pyrazin-1-yl]-acetamid" and insert therefore -- N-(2-carbamimidoyl-[1,2]oxazinan-5-yl)-2-[6-methyl-2-oxo-3-(2-p-tolylethyl-amino)-2H-pyrazin-1-yl]-acetamide --.
Line 25, delete "$PhC(CH_3)_2$," and insert therefor -- $PhC(CH_3)_2CH_2$, --.

UNITED STATES PATENT AND TRADEMARK OFFICE
CERTIFICATE OF CORRECTION

PATENT NO. : 6,476,016 B2
DATED : November 5, 2002
INVENTOR(S) : Wang et al.

It is certified that error appears in the above-identified patent and that said Letters Patent is hereby corrected as shown below:

Column 56,
Lines 30-35, delete the chemical figure

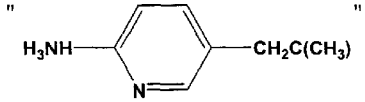

and insert therefor the chemical figure

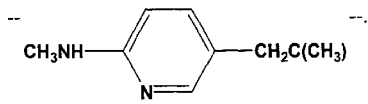

Signed and Sealed this

Third Day of June, 2003

JAMES E. ROGAN
*Director of the United States Patent and Trademark Office*